US006758808B2

(12) United States Patent
Paul et al.

(10) Patent No.: US 6,758,808 B2
(45) Date of Patent: Jul. 6, 2004

(54) SURGICAL INSTRUMENTS FOR STABILIZING A LOCALIZED PORTION OF A BEATING HEART

(75) Inventors: David J. Paul, Scotts Valley, CA (US); Joshua K. Wallin, Sunnyvale, CA (US); Eugene E. Reis, San Jose, CA (US); Alfredo R. Cantu, Fremont, CA (US); Harry L. Green, Santa Cruz, CA (US); Harry Ino, San Jose, CA (US); Charles S. Taylor, San Francisco, CA (US)

(73) Assignee: Cardiothoracic System, Inc., Santa Clara, CA (US)

( * ) Notice: Subject to any disclaimer, the term of this patent is extended or adjusted under 35 U.S.C. 154(b) by 215 days.

(21) Appl. No.: 09/769,964

(22) Filed: Jan. 24, 2001

(65) Prior Publication Data

US 2002/0099268 A1 Jul. 25, 2002

(51) Int. Cl.⁷ .................................................. A61B 1/32
(52) U.S. Cl. ....................................................... 600/229
(58) Field of Search .................. 248/288.51; 403/56, 403/83, 84, 114; 600/206, 210, 229

(56) References Cited

U.S. PATENT DOCUMENTS

| 452,131 | A | 5/1891 | Haughawout |
| 810,675 | A | 1/1906 | Richter |
| 1,706,500 | A | 3/1929 | Smith |
| 2,296,793 | A | 9/1942 | Kirschbaum |
| 2,590,527 | A | 3/1952 | Fluck |
| 2,693,795 | A | 11/1954 | Grieshaber |
| 2,863,444 | A | 12/1958 | Winsten |
| 3,392,722 | A | 7/1968 | Jorgensen |
| 3,466,079 | A | 9/1969 | Mammel |
| 3,683,926 | A | 8/1972 | Suzuki |
| 3,720,433 | A | 3/1973 | Rosfelder |
| 3,783,873 | A | 1/1974 | Jacobs |
| 3,858,926 | A | 1/1975 | Ottenhues |
| 3,882,855 | A | 5/1975 | Schulte et al. |
| 3,912,317 | A | 10/1975 | Ohnaka et al. |

(List continued on next page.)

FOREIGN PATENT DOCUMENTS

| DE | 90 04513 | 6/1990 |
| EP | 0 293 760 A3 | 12/1988 |
| EP | 0 293 760 A2 | 12/1988 |
| EP | 0 293 760 B1 | 12/1988 |
| EP | 0 630 629 | 5/1994 |
| EP | 668 058 A1 | 8/1995 |

(List continued on next page.)

OTHER PUBLICATIONS

09/345,859 Looney et al. filed on Jul. 1, 1999.
09/438,670 Parsons, et al. filed on Nov. 12, 1999.
09/489,274 Brown et al. filed on Jan. 21, 2000.
60/117,333 Looney et al. (provisional) filed on Jan. 24, 1999.
Akins, et al., "Preservation of Interventricular Septal Function in Patients Having Coronary Artery Bypass Graft Without Cardiopulmonary Bypass," American Heart Journal, vol. 107, No, 2, Feb., 1984, pp. 304–309.

(List continued on next page.)

Primary Examiner—Cary E. O'Connor
(74) Attorney, Agent, or Firm—Law Office of Alan W. Cannon

(57) ABSTRACT

Stabilization devices, systems and methods for stabilizing tissue to perform a surgical operation while the heart of the patient continues to beat. A stabilization system including a tissue contact member having a surface adapted to contact the tissue and temporarily maintain the tissue in a relatively immobilized state; and a maneuverable arm attached to the tissue contact member, which includes at least one articulating joint formed by a link having a male articulating surface composed of angled teeth and a female articulating surface having angled trenches adapted to receive the angled teeth.

102 Claims, 18 Drawing Sheets

U.S. PATENT DOCUMENTS

| | | |
|---|---|---|
| 3,916,909 A | 11/1975 | Harold et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Garrick et al. |
| 4,052,980 A | 10/1977 | Grams et al. |
| 4,094,484 A | 6/1978 | Galione |
| 4,096,853 A | 6/1978 | Weigand |
| 4,226,228 A | 10/1980 | Shin et al. |
| 4,230,119 A | 10/1980 | Blum |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,829,985 A | 5/1989 | Couetil |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,925,443 A | 5/1990 | Heilman et al. |
| 4,949,707 A | 8/1990 | LeVahn et al. |
| 4,955,896 A | 9/1990 | Freeman |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,131,905 A | 7/1992 | Grooters |
| 5,133,724 A | 7/1992 | Wilson, Jr. et al. |
| 5,159,921 A | 11/1992 | Hoover |
| RE34,150 E | 12/1992 | Santilli, deceased et al. |
| 5,167,223 A | 12/1992 | Koros et al. |
| 5,171,254 A | 12/1992 | Sher |
| 5,192,070 A | 3/1993 | Nagai et al. |
| 5,231,974 A | 8/1993 | Giglio et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,467,763 A | 11/1995 | McMahon et al. |
| 5,484,391 A | 1/1996 | Buckman, Jr. et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,651,378 A | 7/1997 | Matheny et al. |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,836,311 A | 11/1998 | Borst et al. |
| 5,846,187 A | 12/1998 | Wells et al. |
| 5,846,193 A | 12/1998 | Wright |
| 5,846,194 A | 12/1998 | Wasson et al. |
| 5,865,730 A | 2/1999 | Fox et al. |
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A * | 5/1999 | Corey Jr. et al. ........ 248/276.1 |
| 5,906,607 A | 5/1999 | Taylor et al. |
| 5,908,382 A | 6/1999 | Koros et al. |
| 5,913,876 A | 6/1999 | Taylor et al. |
| 5,927,284 A | 7/1999 | Borst et al. |
| 5,944,658 A | 8/1999 | Koros et al. |
| 5,944,736 A | 8/1999 | Taylor et al. |
| 5,947,125 A | 9/1999 | Benetti |

| | | |
|---|---|---|
| 5,947,896 A | 9/1999 | Sherts et al. |
| 5,957,835 A | 9/1999 | Anderson et al. |
| 5,967,972 A | 10/1999 | Santilli et al. |
| 5,967,973 A | 10/1999 | Sherts et al. |
| 5,976,080 A | 11/1999 | Farascioni |
| 5,976,171 A | 11/1999 | Taylor |
| 5,984,865 A | 11/1999 | Farley et al. |
| 5,984,867 A | 11/1999 | Deckman et al. |
| 6,007,486 A | 12/1999 | Hunt et al. |
| 6,007,523 A | 12/1999 | Mangosong |
| 6,010,531 A | 1/2000 | Donlon et al. |
| 6,013,027 A | 1/2000 | Khan et al. |
| 6,015,378 A | 1/2000 | Borst et al. |
| 6,017,304 A | 1/2000 | Vierra et al. |
| 6,019,722 A | 2/2000 | Spence et al. |
| 6,027,476 A | 2/2000 | Sterman et al. |
| 6,029,671 A | 2/2000 | Stevens et al. |
| 6,030,340 A | 2/2000 | Maffei et al. |
| D421,803 S | 3/2000 | Koros et al. |
| 6,032,672 A | 3/2000 | Taylor |
| 6,033,362 A | 3/2000 | Cohn |
| 6,036,641 A | 3/2000 | Taylor et al. |
| 6,042,539 A | 3/2000 | Harper et al. |
| 6,050,266 A | 4/2000 | Benetti et al. |
| 6,063,021 A | 5/2000 | Hossain et al. |
| 6,071,295 A | 6/2000 | Takahashi |
| 6,099,468 A | 8/2000 | Santilli et al. |
| 6,102,853 A | 8/2000 | Scirica et al. |
| 6,102,854 A | 8/2000 | Carfier et al. |
| 6,110,187 A | 8/2000 | Donlon |
| 6,139,492 A | 10/2000 | Vierra et al. |
| 6,149,583 A | 11/2000 | Vierra et al. |
| 6,183,486 B1 | 2/2001 | Snow et al. |
| 6,190,311 B1 | 2/2001 | Glines et al. |
| 6,193,652 B1 | 2/2001 | Berky et al. |
| 6,200,263 B1 | 3/2001 | Person |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,231,585 B1 | 5/2001 | Takahashi et al. |
| 6,251,065 B1 | 6/2001 | Kochamba et al. |
| 6,264,605 B1 | 7/2001 | Scirica et al. |
| 6,315,717 B1 | 11/2001 | Benetti et al. |
| 6,338,738 B1 * | 1/2002 | Bellotti et al. ............... 606/232 |
| 6,346,077 B1 | 2/2002 | Taylor et al. |
| 6,350,229 B1 | 2/2002 | Borst et al. |
| 6,371,910 B1 | 4/2002 | Zwart et al. |
| 6,375,611 B1 | 4/2002 | Voss et al. |
| 6,394,951 B1 | 5/2002 | Taylor et al. |
| 6,398,726 B1 | 6/2002 | Romans et al. |
| 6,406,424 B1 | 6/2002 | Williamson et al. |
| 6,447,443 B1 | 9/2002 | Keogh et al. |
| 6,458,079 B1 | 10/2002 | Cohn et al. |
| 6,464,629 B1 | 10/2002 | Boone et al. |
| 6,464,630 B1 | 10/2002 | Borst et al. |
| 6,468,265 B1 | 10/2002 | Evans et al. |
| 6,478,029 B1 | 11/2002 | Boyd et al. |
| 6,478,729 B1 | 11/2002 | Rogers et al. |
| 6,482,151 B1 | 11/2002 | Vierra et al. |
| 6,494,211 B1 | 12/2002 | Boyd et al. |
| 6,503,245 B2 | 1/2003 | Palmer et al. |
| 6,506,149 B2 | 1/2003 | Peng et al. |
| 6,537,212 B2 | 3/2003 | Sherts et al. |
| 6,565,508 B2 | 5/2003 | Scirica et al. |
| 6,592,573 B2 | 7/2003 | Castaneda et al. |
| 6,607,479 B1 | 8/2003 | Kochamba et al. |
| 6,610,008 B1 | 8/2003 | Spence et al. |
| 6,610,009 B2 | 8/2003 | Person |

FOREIGN PATENT DOCUMENTS

| | | |
|---|---|---|
| EP | 0 993 806 A2 | 4/2000 |
| FR | 473451 | 1/1915 |
| GB | 168216 | 9/1921 |
| GB | 2 233 561 A | 1/1991 |
| GB | 2 267 827 A | 12/1993 |
| WO | WO 87/04081 | 7/1987 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A3 | 9/1997 |
| WO | WO 97/32514 A2 | 9/1997 |
| WO | WO 97/40752 | 11/1997 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

Ancalmo, N. and J. L. Ochsner: "A Modified Sternal Retractor," Ann. Thorac, Surg. 21 (1976) 174.

Angelini, G.D., M.D. et al., "Fiber–Optic Retractor for Harvesting the Internal Mammary Artery," Ann. Thorac. Surg. (1990; 50:314–5).

Angelini, G.D., M.D., "Simple, Inexpensive Method of Heart Retraction During Coronary Artery Bypass Surgery," Ann. Thora. Surg 46:46–247, Aug. 1988.

Anstadt, M.D., et al., "Direct Mechanical Ventricular Actuation for Cardiac Arrest in Humans," Chest, vol. 100, No. 1, Jul. 1991.

Antinori, C. et al., "A Method of Retraction During Reoperative Coronary Operations Using the Favaloro Retractor," The Society of Thoracic Surgeons: 1989.

Archer, DO, et al., "Coronary Artery Revascularization Without Cardiopulmonary Bypass," Texas Heart institute Journal, vol. 11, No. 1, Mar. 1984, pp. 52–57.

Arom, K.V., et al., "Mini–Sternotomy for Coronary Artery Bypass Grafting," The Annals of Thoracic Surgery 1996; 61:1271–2.

Arom, K.V., et al., "Mini–Sternotomy for Coronary Artery Bypass Grafting," The Annals of Thoracic Surgery 1996; 62:1884–85.

Ballantyne, M.D., et al., "Delayed Recovery of Severally 'Stunned' Myocardium with the Support of a Left Ventricular Assist Device After Coronary Artery Bypass Graft Surgery," Journal of the American College of Cardiology, vol. 10, No. 3, Sep. 1987, pp. 710–712.

Bedellino, M.M., et al., "The Cardiac Rag—Simple Exposure of the Heart," Texas Heart Institute Journal, vol. 15, No. 2, 1988, 134–35.

Beg, R.A., et al., "*Internal Mammary Retractor,*" Ann Thorac, Surg., vol. 39, No. 1, pp. 286–287, Jan. 1985.

Benetti, et al., "*Direct Coronary Surgery with Saphenous Vein Bypass Without Either Cardiopulmonary Bypass or Cardiac Arrest,*" The Journal of Cardiovascular Surgery, vol. 26, No. 3, May–Jun., 1985, pgs. 217–222.

Benetti, et al., "*Direct Myocardial Revascularization Without Extracorporeal Circulation,*" Chest, vol. 100, No. 2 Aug., 1991, pgs. 312–316.

Benetti, J., et al., "*A Single Coronary Artery Bypass Grafting—A Comparison Between Minimally Invasive Off Pump Techniques and Conventional Procedures,*" European Journal of Cardio–Thoracic Surgery, 14 (Supp. I) (1998) S7–S12.

Borst, et al., "*Coronary Artery Bypass Grafting Without Cardiopulmonary Bypass and Without Interruption of Native Coronary Flow Using a Novel Anastomosis Site Restraining Device ("Octopus"),*" J Am Coll Cardiol, May 1996, vol. 27, No. 6, pgs. 1356–1364.

Borst, et al., "*Regional Cardiac Wall Immunobilization for Open Chest and Closed Chest Coronary Artery Bypass Grafting on the Beating Heart; 'Octopus' Method,*" Circulation, Oct. 15, 1995, vol. 92, No. 8, Supplement 1, 1–117.

British Heart Journal, "Coronary Surgery Without Cardiopulmonary Bypass," pgs. 203–205, 1995.

Buffolo, et al., "*Direct Myocardial Revascularization Without Cardiopulmonary Bypass,*" Thorac. Cardiovasc. Surgeon, 33 (1985) pgs. 26–29.

Bugge, M., "*A New Internal mammary Artery Retractor,*" Thorac. Cardiovasc Surgeon 38, pgs. 316–317 (1990).

Calafiore, A. M., et al., "*Minimally Invasive Coronary Artery Bypass Grafting,*" The Annals of Thoracic Surgery, 62:1545–8, 1996.

Campalani et al., "A New Self–Retaining Internal Mammary Artery Retractor." *J. Cardiovas. Surg.,* vol. 28. (1987).

Cartier, R, MD., "*Triple Coronary Artery Revascularization on the Stabilized Beating Heart: Initial Experience,*" Montreal Heart Institute, CJS, vol. 41, No. 4, pgs. 283–288, Aug. 1998.

Chaux, A. and C. Blanche, "*A New Concept in Sternal Retraction: Applications for Internal Mammary Artery Dissection and Valve Replacement Surgery,*" Ann. Thorac. Surg. 42, pgs. 473–474, Oct. 1986.

Cooley, D.A., "*Limited Access Myocardial Revascularization,*" Texas Heart Institute Journal, pgs. 81–84, vol. 23, No. 2, 1996.

*Correspondence and Brief Communications,* Archives of Surgery—volume 115, 1136–37, Sep. 1980.

Cremer, J, MD, "*Off–Bypass Coronary Bypass Grafting Via Minithoracotomy Using Mechanical Epicardial Stabilization,*" The Annals of Thoracic Surgery, 63:S79–83, 1997.

Delacroix–Chevalier Surgical Instruments, IMA Saving Packages Brochure.

DelRossi, A J and Lemole, GM, "*A New Retractor to Aid in Coronary Artery Surgery,*" The Annals of Thoracic Surgery, vol. 36, No. 1, 101–102, Jul. 1983.

Fanning, MD., "*Reoperative Coronary Artery Bypass Grafting Without Cardiopulmonary Bypass,*" The Annals of Thoracic Surgery, vol. 55, No. 2, Feb. 1993, pgs. 486–489.

Favaloro, M.D., et al, "*Direct Myocardial Revascularization by Saphenous Vein Graft,*" The Annals of Thoracic Surgery, vol. 10, No. 2, Aug. 1970.

Fonger, et al., "*Enhanced Preservation of Acutely Ischemic Myocardium with Transeptal Left Ventricular Assist,*" The Annals of Thoracic Surgery, vol. 57, No. 3, Mar. 1994, pgs. 570–575.

Gacioch, et al., "*Cardiogenic Shock Complicating Actue Myocardial Infarction: The Use of Coronary Angioplasty and the Integracion of the New Support Device into Patient Management,*" Journal of the American College of Cardiology, vol. 19, No. 3, Mar. 1, 1992.

Green, GE., "*Technique of Internal Mammary–Coronary Artery Anastomosis,*" The Journal of Cardiovascular Surgery, 78:455–79, 1979.

Groopman, J., "*Heart Surgery, Unplugged; Making the Coronary Bypass Safer, Cheaper, and Easier,*" The New Yorker, Jan. 11, 1999, pgs. 43–46, 50–51.

Guzman, F. M.D., "*Transient Radial Nerve Injury Related to the Use of A Self Retraining Retractor for Internal Mammary Artery Dissection,*" J. Cardiovasc. Surg. 30, 1989, pgs. 1015–1016.

Hasan, RI, et al., "*Technique of Dissecting the Internal Mammary After Using the Moussalli Bar,*" European Journal of Cardiothoracic Surgery, 4:571–572, 1990.

Itoh, Toshiaki, M.D., et al., "*New Modification of a Mammary Artery Retractor,*" Ann. Thorac. Surg. 9, 1994; 57:1670–1.

Izzat, FRCS, et al., "*Cardiac Stabilizer for Minimally Invasive Direct Coronary Artery Bypass,*" Elsevier Science Inc., 1997 by the Society of Thoracic Surgeons.

Japanese Article "*Heart Retractor*".

Japanese Journal of Thoracic Surgery, vol. 42, No. 2, 1989.

Kazama, S. et al., "*Fabric Heart Retractor for Coronary Artery Bypass Operations,*" The Annals of Thoracic Surgery, 55:1582–3, 1993.

Kolessov, M.D., "*Mammary Artery–Coronary Artery Anastomosis as Method of Treatment for Angina Pectoris,*" Thoracic and Cardiovascular Surgery, vol. 54, No. 4, Oct., 1967, pgs. 535–544.

Konishi, T. MD, et al., "*Hybrid–Type Stabilizer for Off–Pump Directed Coronary Artery Bypass Grafting,*" Annals of Thoracic Surgery 66;961–2, 1998.

Kresh, et al., "*Heart–Mechanical Assist Device Interaction,*" Trans. Am. Soc. Artif. Intern. Organs, vol. XXXII, 1986, pgs. 437–443.

Lavergne, et al., "*Transcatheter Radiofrequency Ablation of Atrial Tissue Using a Suction Catheter,*" PACE, vol. 12, Jan. 1989, Part II, pgs. 177–186.

Lonn, M.D., et al. "*Coronary Artery Operation Supported by the Hemopump: An Experimental Study on Pigs,*" The Annals of Thoracic Surgery, vol. 58, No. 1, Jul. 1994, pgs. 516–523.

Matsuura, A. MD, et al., "*A New Device for Exposing the Circumflex Coronary Artery,*" The Annals of Thoracic Surgery, 59:1249–50, 1995, pgs. 1249–1250.

McGee, et al. "*Extended Clinical Support with an Implantable Left Ventricular Assist Device,*" Trans. Am Soc. Artif. Intern. Organs, vol. XXXV, 1989, pgs. 614–616.

McKeown, P.P. et al., "*A Modified Sternal Retractor for Exposure of the Internal Mammary Artery,*" Ann. Thorac. Surg. 32 (1981) 619.

Ochsner, JL, et al., "*Surgical Management of Diseased Intracavitary Coronary Arteries,*" The Annals of Throacic Surgery, vol. 38, No. 4, Jul., pgs. 356–362, Oct. 1984.

Parsonnet, V. MD, et al., "*Graduated Probes for Coronary Bypass Surgery,*" The Journal of Thoracic and Cardiovascular Surgery, vol. 68, No. 3, 424–26 (Sep. 1974).

Parsonnet, V. MD, et al., "*Self—Retaining Epicardial Retractor for Aortocoronary Bypass Surgery,*" The Journal of Thoracic and Cardiovascular Surgery, 629–30 1979.

Perrault, L. et al., "*Snaring of the Target Vessel in Less Invasive Bypass Operations Does Not Cause Endothelial Dysfunction,*" The Society of Thoracic Surgeons, pgs. 751–755, 1997.

Pfister, et al., "*Coronary Artery Bypass Without Cardiopulmonary Bypass,*" The Annals of Thoracic Surgery, vol. 54, No. 6, Dec. 1992, pgs. 1085–1092.

Phillips, Steven J., M.D. et al., "*A Versatile Retractor for Use in Harvesting the Internal Mammary Artery and Performing Standard Cardiac Operations,*" J. Thorac. Cardiovasc. Surg. (1989; 97:633–5).

Pilling Surgical Instruments, A Rusch International Company Brochure.

Pittman, John, M.D., et al., "*Improved Visualization of the Internal Mammary Artery with a New Retractor System,*" Ann. Thorac. Surg., 1989; 48:869–70.

Riahi, et al., "*A Simple Technique and Device to Provide a Bloodless Operative Field in Coronary Artery Surgery Without Cross–Clamping the Aorta,*" The Journal of Thoracis and Cardiovascular Surgery, vol. 66, No. 6., Dec. 1973, pgs. 974–78.

Richenbacher, M.D., et al., "*Current Status of Cardiac Surgeyr: A 40–Year Review,*" Journal of American College of Cardiology, vol. 14, No. 3, pgs. 535–544.

Robicsek, F., "*Aortic Spoon–Jaw Clamp for Aorta–Saphenous Vein Anastomosis,*" Journal of Cardiac Surgery, 10:583–585, 1995.

Robinson, et al., "*A Minimally Invasive Surgical Method for Coronary Revascularization—Preliminary Experience in Five Patients,*" Circulation, Oct. 15, 1995, vol. 92, No. 8, 1–176.

Rousou, J. et al., "*Cardiac Retractor for Coronary Bypass Operations,*" The Society of Throacic Surgeons, pgs. 52:877–78, 1991.

Roux, D. MD. et al., "*New Helper Instrument in Cardiac Surgery,*" The Annals of Thoracic Surgery, 48: 595–6, 1989.

Roux, D., M.D. et al., "*Internal Mammary Artery Dissection: A Three Dimensional Sternal Retractor,*" J. Cardiovasc. Surg., 1989; 30:996–7.

Ruzevich et al. "*Long–Term Follow–up of Survivors of Postcardiotomy Circulatory Support,*" Trans. Am. Soc. Artif. Intern. Organs, vol. XXXIV, 1988, pgs. 116–124.

Scholz, et al. "*Transfemoral Placement of the Left Ventricular Assist Device 'Hemopump' During Mechanical Resuscitation,*" Thoracic and Cardiovascular Surgeon, vol. 38 (1990) pgs. 69–72.

Stevens, et al., "*Closed Chest Coronary Artery Bypass With Cardioplegic Arrest in the Dog,*" 67$^{th}$ Scientific Session, 238, I–251.

Trapp and R. Bisarya, "*The Use or Not to Use the Pump Oxygenator in Coronary Bypass Operations,*" The Annals of Thoracic Surgery, vol. 19, No. 1, Jan. 1975, pgs. 108–109.

Trapp, et al., "*Placement of Coronary Artery Bypass Graft without Pump Oxygenator,*" Journal of the Society of Thoracic Surgeons and the Southern Thoracic Surgeons Assn. vol. 19, No. 1, Jan. 1975.

USSC Cardiovascular Thora–Lift J, United States Surgical Corporation, Norwalk, Connecticut, Product Brochure.

Vigano, M., "*Tecnica Operatoria Operatoria,*" Minerva Cardioangiologica, vol. 23–N. 6–7 (1975).

Vincent, J.G., "*A Compact Single Post Internal Mammary Artery Dissection Retractor,*" Eur. J. Cardio–Thor. Surg. 3 (1989).

Westaby, S. et al., "*Less Invasive Coronary Surgery: Consensus From the Oxford Meeting,*" The Annals of Thoracic Surgery, 62:924–31, 1996.

Zumbro, et al., "*A Prospective Evaluation of the Pulsatile Assist Device,*" The Annals of Throacic Surgery, vol. 28, No. 2, Aug., 1979, pgs. 269–273.

\* cited by examiner

SURGICAL INSTRUMENTS FOR STABILIZING A LOCALIZED PORTION OF A BEATING HEART

FIELD OF THE INVENTION

The present invention relates generally to surgical instruments, and more particularly to surgical instruments useful for stabilizing a portion of a beating heart during coronary surgery.

BACKGROUND OF THE INVENTION

Surgeries to treat heart disease, and particularly narrowing and/or blockages in the coronary arteries that supply oxygen and nutrients to the heart, are increasing in numbers due to the aging of the population in America and other developed nations, as well as the diets in such nations and a variety of other factors. Classical open heart surgery techniques have been performed to bypass coronary artery blockages, often by rerouting the blood flow around the blockage, using a graft, such as from the saphenous vein. Another technique involves supplying blood to a location downstream of a blockage by anastomosing another artery to the coronary artery, e.g. a mammary artery.

These techniques have traditionally been performed only after stopping the beating of the heart, and connecting the patient's circulatory system to a heart-lung bypass machine, which supplies the patient with the needed circulatory and oxygenation functions while the heart is stopped and the surgeries are being performed. All during this process, blood flow into the chambers of the heart is bypassed. Various post-procedure side effects have been associated with the use of the bypass machine, some of which can be severe. For example, the mechanical damage to the blood tissues that results from the pumping action of the bypass machine has been associated with increased risks of postoperative embolisms and stroke. To alleviate the increased postoperative risks associated with bypass surgery, beating heart surgeries are becoming increasingly prevalent, in which the heart beat is not stopped, but maintains the circulatory flow of blood, oxygen and nutrients throughout the surgery. A bypass machine is not used.

Methods and apparatus for performing a coronary artery bypass graft (CABG) procedure on the beating hear are described in U.S. Pat. Nos. 5,894,843 and 5,727,569 to Benetti et al., the entireties of which are herein incorporated by reference thereto. In a typical CABG procedure, a blocked or restricted portion of a coronary artery, which normally supplies blood to some portion of the heart, is bypassed using a source vessel or a graft vessel to re-establish blood flow to the artery downstream of the blockage or restriction. This procedure requires a surgeon to create a fluid connection, or anastomosis, between the source or graft vessel and an arteriotomy or incision in the coronary artery. The formation of an anastomosis between two such vessels is a particularly delicate procedure, which requires precise placement of sutures in the tissue surrounding the arteriotomy and the source or graft vessel. An anastomosis between vessels of these dimensions is tedious during a stopped-heart procedure, but during a beating heart procedure it is markedly even more difficult.

As could be expected, it is very important that the target site for the anastomosis be stabilized to remain substantially motionless, even while the remainder of the heart tissue remains beating all around the target site. To this end, a number of devices have been developed which are directed to stabilizing a target site on the beating heart for the purpose of completing a cardiac surgical procedure, such as completing an anastomosis. Representative devices useful for stabilizing a beating heart are described, for example, in U.S. Pat. Nos. 5,894,843; 5,727,569; 5,836,311 and 5,865,730.

As beating heart procedures have evolved, new challenges have arisen in the design and engineering of the stabilization devices. The heart is typically accessed by way of a surgical incision such as a sternotomy or a thoracotomy. Such an incision, even with the use of one or more retractors leaves only a limited opening space within which to perform the surgical procedures. Often one ore more of the blocked or restricted arteries are located a good distance away from the access incision, requiring the stabilization device to traverse a longer and more tortuous path than if the artery were located so as to be directly exposed to the access incision. Also, distant locations can be such that the stabilization device must engage the surface of the heart at difficult angular relationships or orientations. Under the most severe conditions, devices which operate to provide a mechanical force to stabilize the beating heart can encounter difficulty maintaining mechanical traction against the surface of the heart if they are not sufficiently maneuverable, and devices which utilize suction or vacuum to engage the heart can have a difficult time maintaining a vacuum seal against the heart tissue for the same reason.

Even a device that is extremely maneuverable so as to be able to place the stabilizing portion of the device at many locations on the heart may not have a sufficiently small size of low profile to be an effective device. Since the working space provided by the incision opening is quite limited, it is desirable to make the stabilization device as small and low profile as possible to maintain maximum working space, as well as visibility for the surgeon.

In view of the foregoing, it would be desirable to have methods and devices for stabilizing the beating heart that improve upon the maneuverability of the existing devices while maintaining or decreasing the amount of space that is occupied thereby, to provide the surgeon with more working space, better visibility and to make the overall procedure easier by making the operation of the stabilization device easier and more effective.

SUMMARY OF THE INVENTION

The present invention will be primarily described for use in stabilizing the beating heart during a surgical procedure, but the invention is not limited thereto, and may be used in other surgical procedures. Described herein is a stabilization system including a tissue contact member having a surface adapted to contact the tissue and temporarily maintain the tissue in a relatively immobilized state; and a maneuverable arm attached to the tissue contact member, which includes at least one articulating joint formed by a link having a male articulating surface composed of angled teeth and a female articulating surface having angled trenches adapted to receive the angled teeth. This type of articulating joint moves in one degree of freedom directed by the angled teeth sliding against the angled trenches.

In an example described, the maneuverable arm comprises a plurality of the above-described articulating joints. Further, one or more rotational joints may be provided, each formed by a link having a male articulating surface and a link having a female articulating surface, which are positioned for relative rotation in a plane perpendicular to a longitudinal axis of the maneuverable arm. The rotational joints, together with the articulating joints impart maneuverability in three dimensions to the maneuverable arm.

In an example described, a first rotational joint is provided intermediate the articulating joints and a second rotational joint is positioned at or near a proximal end of the maneuverable arm.

A low profile mount is provided which is connected at a proximal end portion of the maneuverable arm. The mount includes a first mount portion and a second mount portion, which is pivotally connected to the first mount portion. The first mount portion may be integral with a male or female articulating surface of a rotational joint that it then forms a part of at the proximal end of the maneuverable arm. The second mount portion is pivotal away from the first mount portion to position the mount over a fixed object, or to release the mount from the fixed object. The mount portion also allows the stablization system to be slid along a rail on a fixed object to which it is mounted. The second mount portion is pivotable toward the first mount portion to fix the mount on the fixed object.

The mount may further comprise a locking mechanism adapted to lock the second mount portion to the first mount portion in a closed position upon pivoting the second mount portion toward the first mount portion. The closed position is configured to lock the mount on the fixed object. The fixed object may be a sternal retractor, for example, or other object, which is stationary relative to the moving tissue. The mount portions may each further include a rail grip adapted to engage one side of a rail on a sternal retractor. The locking mechanism may include a living hinge formed in one of the first and second mount portions and a pin extending transversely on the other of the first and second mount portions, the pin being adapted to snap fit into the living hinge.

A cable passes internally through each of the articulating joints, rotational joints and mount of the device. The cable is further attached to a tensioning mechanism proximally of the mount. The tensioning mechanism may include a screw mechanism and a knob. The screw mechanism has a first threaded component having a first set of threads and a second threaded component having a second set of threads adapted to mate with the first set of threads. The first threaded component is fixed to the cable and the knob is adapted to torque the second threaded component with respect to the first threaded component. The screw mechanism is adapted to lock the first and second mount portions together in the closed position, to securely lock the stabilization system on the rail on which it is mounted.

The second threaded component may include a torque limiter having a unidirectional slip clutch, which is engageable with the knob. The knob positively engages the torque limiter for unthreading the second set of threads from the first set of threads, and positively engages the torque limiter for threading the second set of threads on the first set of threads until a predetermined amount of torque is required to further tension the cable. Upon reaching the predetermined amount of torque during threading, the torque limiter slips with respect to the knob.

The slip clutch may include at least one fin extending from an outer surface of the second threaded member at an angle to a line normal to a tangent line passing through the location from which the fin extends. Each fin is adapted to engage a groove formed in an inner surface of the knob.

The cable includes a stop member fixed to a distal end thereof, such that, upon applying tension to the cable with the tensioning member, the stop member and the tensioning member apply a compressive force to the articulating joints and rotational joints, thereby locking every joint into an assumed orientation.

A coupling mechanism which links the stop member to the tissue contact member, thereby also linking the maneuverable arm to the tissue contact member, is further provided. The coupling member is adapted to lock the tissue contact member in an assumed position when the cable is placed under a sufficient tension to lock the maneuverable arm.

The coupling mechanism may include a ball member fixed to the tissue contact member and a socket member rotatably joined with the stop member and adapted to receive the ball member to form a ball joint. The socket member may further include a slot through a side wall thereof, which terminates in an enlarged opening dimensioned to permit the ball member to pass therethrough. The coupling mechanism may further include a coupling link having arms adapted to lock with the socket member, and an upper abutment surface adapted to abut the stop member. A second coupling link having driving surfaces adapted to contact a distal most link of a distal most articulating joint of the maneuverable arm may also be provided. The second coupling link further includes a lower abutment surface adapted to abut an upper portion of the ball member, wherein, upon tensioning of the cable, the stop member draws the first coupling link and the socket member in a proximal direction, whereby the socket member compresses the ball member against the lower abutment surface.

Optionally, a flexible sleeve positioned over the articulating joints and the rotational joints of the maneuverable arm. The flexible sleeve may comprise an elastomer, such as silicone or dip molded PVC, for example. Preferably, the flexible sleeve comprises a material having a four or six way stretch, such as LYCRA®, or SPANDEX (elastomeric fabric of fibers containing polyurethane), for example.

The tissue contact member is rotatable in three degrees of freedom with respect to the distal end of the maneuverable arm. The tissue contact member may be locked with respect to the maneuverable arm in virtually any position to which the tissue contact member may be maneuvered when in an unlocked state. The locking mechanism simultaneously locks the maneuverable arm in virtually any position to which the maneuverable arm may be maneuvered when in an unlocked state.

The tissue contact member may include a pair of feet extending substantially parallel to one another and adapted to straddle a target site on the tissue. The pair of feet may extend from a common base portion and the common base portion may be angled away from a plane in which the feet substantially extend. Other tissue contact members described herein may be incorporated into the system as described herein. A large variety of tissue contact members may be adapted for use in the stabilizer of the present invention by providing each with a ball member extending therefrom which is adapted to form a ball joint at the distal end of the maneuverable arm.

Tissue contact members which employ negative pressure to aid in the stabilizing function may also be utilized, in one example, each contact member or foot of the tissue contact member includes a thin compliant seal extending around a perimeter of a bottom surface thereof. Each compliant seal may have a tapering thickness, wherein the thickness is greater adjacent the bottom surface of the foot and tapers thinner in a direction extending away from the bottom surface. The compliant seal may have a tapering length, forming a variable seal, wherein the length measures a distance that the seal extends away from the bottom surface. The seal may have a greater length near the proximal end of the foot than near the distal end of the foot. The tissue contact members, whether employing negative pressure or not are substantially rigid, as described herein, although malleable contact members may also be employed.

In one example of a tissue contact member that employs negative pressure, the tissue contact member includes a manifold base interconnected with a pair of feet. The manifold base is substantially hollow and has a pair of fittings extending therefrom, on which the feet are mounted. Each foot is independently rotatable about the respective fitting, with respect to the manifold base. Each foot has a hollow interior defining a vacuum chamber, with each vacuum chamber having a first opening adapted to engage at least a portion of the tissue and a second opening fluidly coupled with an opening through the respective fitting extending from the manifold base.

Each vacuum chamber may further include channels formed on an upper interior surface of the foot. The channels may be aligned substantially parallel to one another and extend in a direction from the proximal end to the distal end of the foot. A deep channel may be formed near the distal end of each foot, to fluidly communicate with the opening through the respective fitting.

Each foot may have an asymmetrical transverse cross-section. A porous filter may be provided to cover at least a portion of the channels in each vacuum chamber. The porous filter may be integrally molded with the thin compliant seal on each foot. Each seal may be provided with one or more grooves to further enhance the flexibility thereof.

A rotatable fitting may be mounted to the manifold base, thereby providing a rotational connection between a vacuum line and the manifold base adapted to snap fit over said third fitting, said rotatable fitting further comprising an inlet tube configured for connecting with a vacuum line, whereby the vacuum line is rotatably mounted to said manifold base.

Other novel tissue contact members are also described herein, including one having a pair of feet comprising an extremely low profile structural member and a thin compliant seal extending from a bottom perimeter of the structural member.

A tensioning mechanism for applying tension to a cable passing through a maneuverable surgical instrument is described as comprising a screw mechanism and a knob. Alternatively, a one-step lock mechanism may be employed that uses a coarser thread, or camming surfaces to lock/unlock the mechanism with a single partial turn. The screw mechanism has a first threaded component having a first set of threads and a second threaded component having a second set of threads adapted to mate with the first set of threads. The first threaded is fixed to the cable and the knob is adapted to torque the second threaded component with respect to the first threaded component.

The second threaded component may include a torque limiter, which may include a unidirectional slip clutch engaging that engages the knob up to a predetermined torque level and then slips with respect thereto, thereafter.

A device for providing additional stabilization to tissue already in contact with a primary stabilization member is disclosed which includes at least one tissue contact member adapted to be placed on the tissue in an area bounded by primary tissue contact members, and a connecting member extending from the at least one tissue contact member and adapted to be hand held or fixed to a relatively immovable object. The device is also included with a primary stabilization device in a stabilization system.

A method of stabilizing tissue at a location of a target site at which an operative procedure is to be performed is described to include contacting the tissue in the vicinity of the location with a primary stabilizing instrument to stabilize the general vicinity of the location; and contacting the tissue in a location between the location where the primary stabilizing instrument contacts the tissue and the target site, to further stabilize the target site.

The method may further include fixing each of the primary and second stabilizing instrument to the same or different relatively immovable objects after tissue contact has been established. The secondary stabilizing instrument may alternatively be fixed to the primary stabilizing instrument or hand held.

These and other objects, advantages, and features of the invention will become apparent to those persons skilled in the art upon reading the details of the instruments and methods as more fully described below.

BRIEF DESCRIPTIONS OF THE DRAWINGS

DETAILED DESCRIPTION OF THE INVENTION

Figure 1:
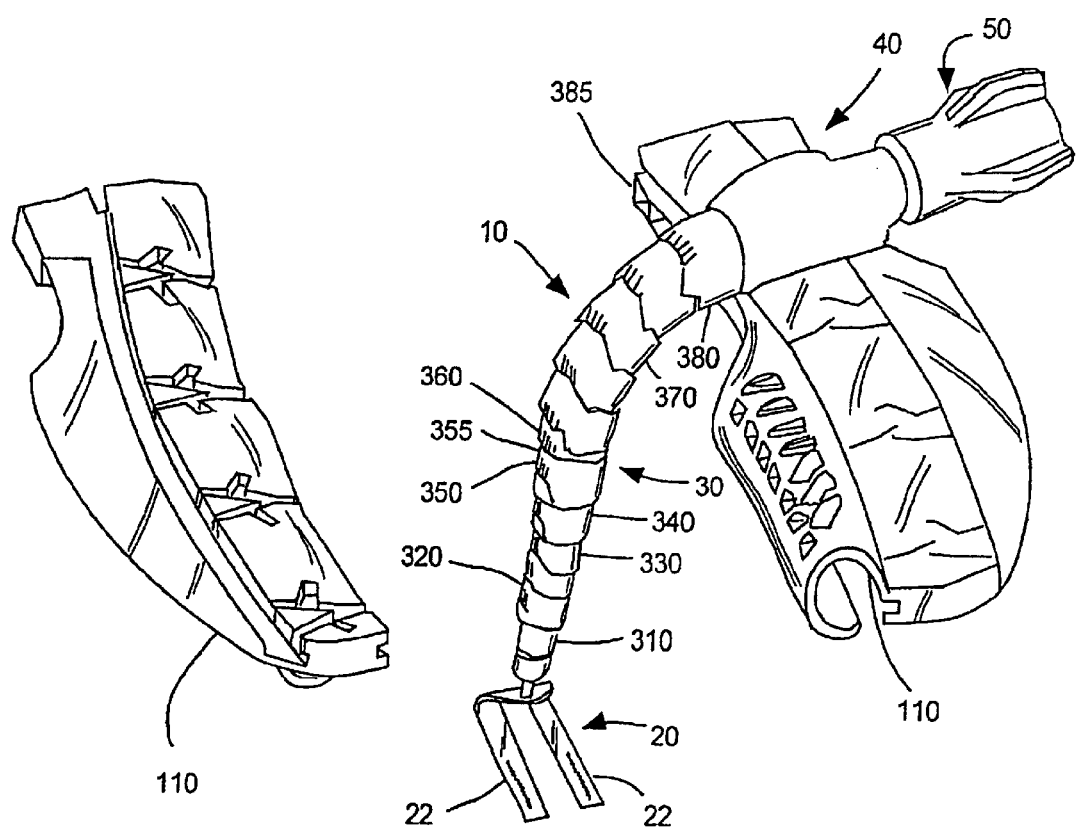
FIG. 1 is a perspective view illustrating an example of a stabilizing instrument mounted to a rail of a retractor arm according to the present invention.

Before the present instruments and methods are described, it is to be understood that this invention is not limited to particular stabilizers, retractors or other devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a joint" includes a plurality of such joints and reference to "the trench" includes reference to one or more trenches and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The instruments and methods of the present invention may be used for stabilization of a beating heart during a coronary artery bypass graft (CABG) procedure in which the bypass of a narrowed or blocked vessel is performed without application of cardioplegia to the patient and without cardiopulmonary bypass. The instruments and methods enable the contacting of the heart and relative stabilization at and in the surrounding area of the portion of the heart contacted, to make it possible to perform delicate surgical tasks in that area.

Although the instruments of the present invention may be used for stabilizing tissue in other applications, they are most advantageously employed in a CABG procedure in combination with a sternal retractor used to provide an opening in the chest for direct access to the heart. While it would be apparent to one of ordinary skill in the art that the present instruments could be employed separately from a retractor, they are nonetheless adapted to be mounted to a retractor to provide a desirable base of stability. However, other objects of fixation could be utilized if necessary, as known in the art. Further, other types of retractors than a sternal retractor might be employed to achieve access to the heart, and such other retractors (e.g., retractor used in thoracotomy, and other rib separators) could also serve as a base to which the present instruments could be fixed.

Further, the instruments of the present invention could be advantageously used for their stabilization capabilities in a stopped heart procedure, including procedures employing cardiopulmonary bypass. However, the present instruments are particularly advantageous in beating heart procedures. Although the present instruments may access and stabilize the beating heart in a number of surgical contexts involving various incisions and surgical approaches to the heart as are known in the art, the instruments described herein are most advantageously employed in CABG procedures where the heart is accessed through only one or two minimally invasive incisions in the chest. Particularly, methods involving a sternal retractor are described.

Although the particular source vessel and target artery of a surgical anastomosis performed in a beating heart CABG procedure are determined clinically, one common procedure involves an anastomosis which forms a connection between the left internal mammary artery (LIMA) as the source artery, and the left anterior descending artery (LAD) as the target artery. Another common procedure involves anastomosing a saphenous vein graft proximally to the aorta and distally to a target artery, post blockage location. The anastomosis procedure in either case (as well as in other less common varieties of anastomosis procedures) is a delicate and exacting procedure which requires the installation of very fine sutures around the entire perimeter of the source vessel or graft to attach it to the target vessel in a manner that is substantially leak-proof, for the immediate commencement of delivery of blood to the heart via the surgically altered pathway achieved by the procedure.

For this reason, effective stabilization of the anastomosis site is paramount if the surgeon is to effectively perform the suturing task. Also, the working space surrounding the anastomosis site is quite limited, and visibility of the site is also extremely important to the surgeon, who will perform the suturing tasks visually. Thus, instruments involved in the procedure should be minimal in size and place a premium on being located in areas least likely to obstruct the surgeon's view while performing the procedure, while also maintaining sufficient access space for the instruments needed in conducting the suturing and related procedures. The instruments should also be easy to operate and effective at stabilizing a desired area of tissue on the heart. Since this desired area may vary, the instruments should be extremely maneuverable so as to be versatile for use in many, if not all desired target locations on the heart.

The devices of the present invention involve tissue stabilizers which provide superior engagement with the surface of the heart. Tissue stabilizers according to the present invention may have one or more stabilizer feet, which are adjustable as to the orientation of their features which are used to contact the tissue surface, e.g., the surface of the heart. Various types of stabilizer feet may be employed and are described in detail below.

Figure 2:
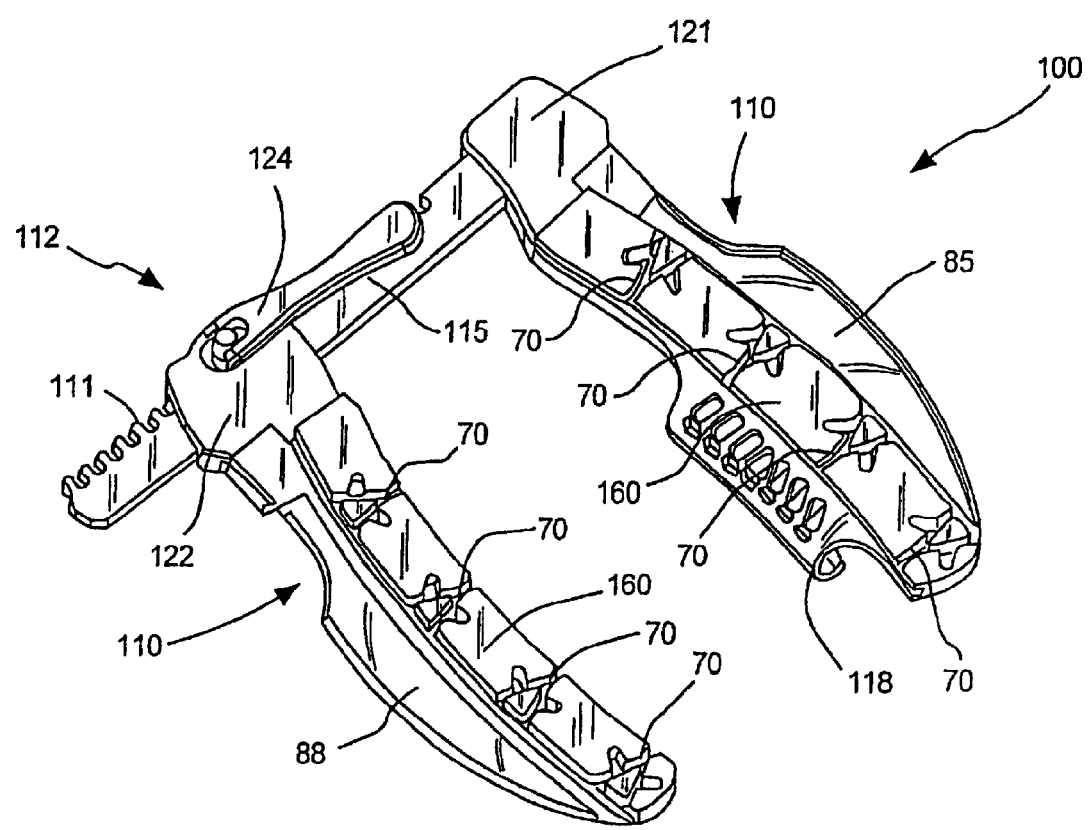
FIG. 2 is a perspective view of a retractor system including the retractor arms shown in FIG. 1.

Referring to the figures in which like reference numerals indicate like elements, an exemplary stabilizer 10 is illustrated in FIG. 1 and is shown mounted to a removable blade portion 110 of a sternal retractor 100 (FIG. 2). As shown in FIGS. 1 and 2, the stabilizer 10 is adapted to be mounted to a retractor assembly 100 for performing a mid-sternal surgical procedure on the beating heart, although the present invention is not limited to such an application, as described above.

Retractor assembly 100 generally includes a pair of opposing blades 110 adapted to engage opposite sides of a sternal incision, or other incision, and a drive mechanism 112 constructed to force the blades 110 apart, thereby driving an opening in the sternum. Using the drive mechanism 112, the sternum may thus be spread to the desired opening, thus providing the desired access and direct visualization of the thoracic cavity. If desired, the heart may be positioned or oriented to best present the target vessels for anastomosis. This positioning may be established, for example, through the strategic placement and tensioning of sutures in the pericardial sac, by appropriately placing the patient in the Trendlenburg position, or by using a heart positioner including a strap or pad or other device, such as a Guidant XPOSE™ device, available from Guidant Corp., Cupertino, Calif., for example.

Once the target vessel is in the desired position, the stabilizer assembly 10, having been mounted to the retractor assembly 100 is manipulated so as to bring at least one component of the stabilizer assembly 10 into contact with the beating heart adjacent the target site of the anastomosis. The surgeon typically applies a stabilizing force to the beating heart via the stabilizer assembly 10 until the desired stabilization if attained, and secures the stabilizer assembly in a fixed orientation to maintain the stabilizing force against the beating heart.

The positioning and fixation of the stabilizer assembly 10 substantially eliminates movement of the heart in the area of the anastomosis, thereby facilitating the surgeon's placement of sutures and related procedural requirements in performing the anastomosis (or other surgical procedure). After the anastomosis has been completed, the stabilizer assembly 10 is released to enable it to be flexibly moved away from contact with the heart.

The retractor assembly 100 shown in FIG. 2 may be used in mid-sternotomy procedures, together with a stabilizer assembly 10 according to the present invention, but is shown for purposes of example only. As noted above, stabilizer assemblies according to the present invention may be used with other types of retractors, or even without a retractor. Retractor assembly 100 includes a drive mechanism 112 to which are mounted a pair of opposing retractor blades 110 adapted for insertion into an incision and for engaging opposite sides of the incision. In the example shown, retractor blades 110 are removable from the drive mechanism 112, although this feature is not required for operation with a stabilizer assembly 10 according to the present invention.

When the heart is accessed by way of an incision through all or a portion of the sternum, the opposing blades 110 may be inserted into the incision and driven apart by operation of the drive mechanism 112 to create an opening and working space for operating on the heart. Typically, the drive mechanism 112 is constructed to spread the opposing blades apart in a generally planar movement, although the separating motion may also have a significant curvilinear or angular component in addition.

The blades 110 may each have one or more channels or engaging members 118 adapted to engage opposite sides of an access incision. Different sizes of blades are available so as to optimize the engagement of the retractor assembly with various sizes and shapes of sternums. Activation of the drive mechanism 112 force apart the first and second platform blades 110 thereby causing engaging members 118 to correspondingly force the incision open to provide access to the desired surgical site. In the example of a sternal approach to the heart, engaging members 118 are adapted to engage each side of the incised sternum to reliably hold and engage the sternum as the sternum is forced open to expose the thoracic cavity and ultimately the heart.

Although any type of drive mechanism which provides the desired separating action of the blades may be suitable, FIG. 2 shows a ratchet or rack arrangement, as is generally known in the art. Rotation of the handle on handle assembly 124 facilitates movement of a moveable housing 124 relative to the bar 115 of the drive mechanism 112, by engaging a pinion (not shown, but mounted to the handle) with the rack teeth 111 on the bar 115 in a cogging manner. This effectively moves the blade 110, that is attached to or mounted on the movable housing 124, toward or away from the other blade 10 that is attached to or mounted on a fixed housing 121 which does not move relative to the bar 115.

In addition to engaging members 118, platform blades 110 (which may be detachable or integrally formed with the drive mechanism 112) may incorporate a wide variety of additional features which enhance the performance of the retractor system. For example, one or both blades may have mounting features to which stabilizer 10, and various other instruments used during the procedure, can be secured. In the case of the stabilizer 10, it is critical to minimize or substantially eliminate the amount of flex and motion attributable to each component and each connection between each component, from the component which engages the beating heart to the component which provides the sternal attachment. To this end, the engaging features 118 which engage the sternum are preferably part of a unitary platform blade structure which also includes mounting features to which a stabilizer and other instruments can be mounted and secured. Since the mounting features and the sternal engaging features are part of the same component, there is no mechanical connection between the two, and the stability of an attached instrument against the forces of a beating heart is greatly improved.

In the example shown, the first and second platform blades 110 include mount features in the form of rails 160. Optionally, a mount feature may also be included on the rack bar 115. The rails 160 allow stabilizer 10 (and other instruments) to be positioned at any desired location along the operable length of either rail. The rails 160 may be oriented substantially perpendicular to the direction of separation of the blades 110, or in a more curvilinear fashion. In this example, the rails 160 extend upwardly from the bodies of the platform blades 110, although they may be formed alternatively as recessed features or in another configuration. However, the upwardly extending configurations are adapted to connect with the stabilizers having connecting features as shown in the examples. Of course, it would be possible to provide stabilizers having connecting features adapted to connect with recessed rails or rails having some other connecting feature.

Stabilizer 10 is a multi-jointed device which provides the flexibility needed to reach less direct surfaces of the heart from the incision opening. Additionally, stabilizer 10 is extremely low profile to maximize the amount of free space available in the opening for use by the surgeon. In the example shown in FIG. 1, stabilizer 10 includes a heart contact member 20 adapted to contact the heart adjacent the site desired to be stabilized. The contact member 20 may include a pair of feet or contact members 22 as shown in FIG. 1, which may be substantially planar, or slightly curved to conform to the shape of the heart, or one or more may have a non-conforming curve to establish a contact between only a portion of the contact member 20 and the beating heart. The shape of the feet 22 and the contact member 20 may be varied depending on the clinical assessment by the surgeon, the design of the remainder of the stabilizer 10, and/or the design of other instruments to be used to complete the anastomosis. Various examples of contact members will be detailed herein as the description proceeds.

Stabilizer 10 further includes a highly maneuverable arm 30 which connects the contact member 20 through a base member 40 to a tightening mechanism 50 at the proximal end of the device. The maneuverable arm 30 includes multiple articulating joints which enable the contact member 20 to be positioned and set at a wide variety of positions, virtually enabling the contact member to be used for any target site in performing anastomoses according to the present invention. The multiplicity of articulating joints allow versatile positioning, and a cable 288 which runs through each of the joints and interconnects them with the tightening mechanism 50, may be tensioned to freeze the selected orientation of the device in a rigid configuration. In this way, the contact member 20 can be maintained at the desired orientation to provide stabilization to that portion of the heart tissue with which it makes contact, as well as the immediately surrounding area.

Figures 3A, 3B:
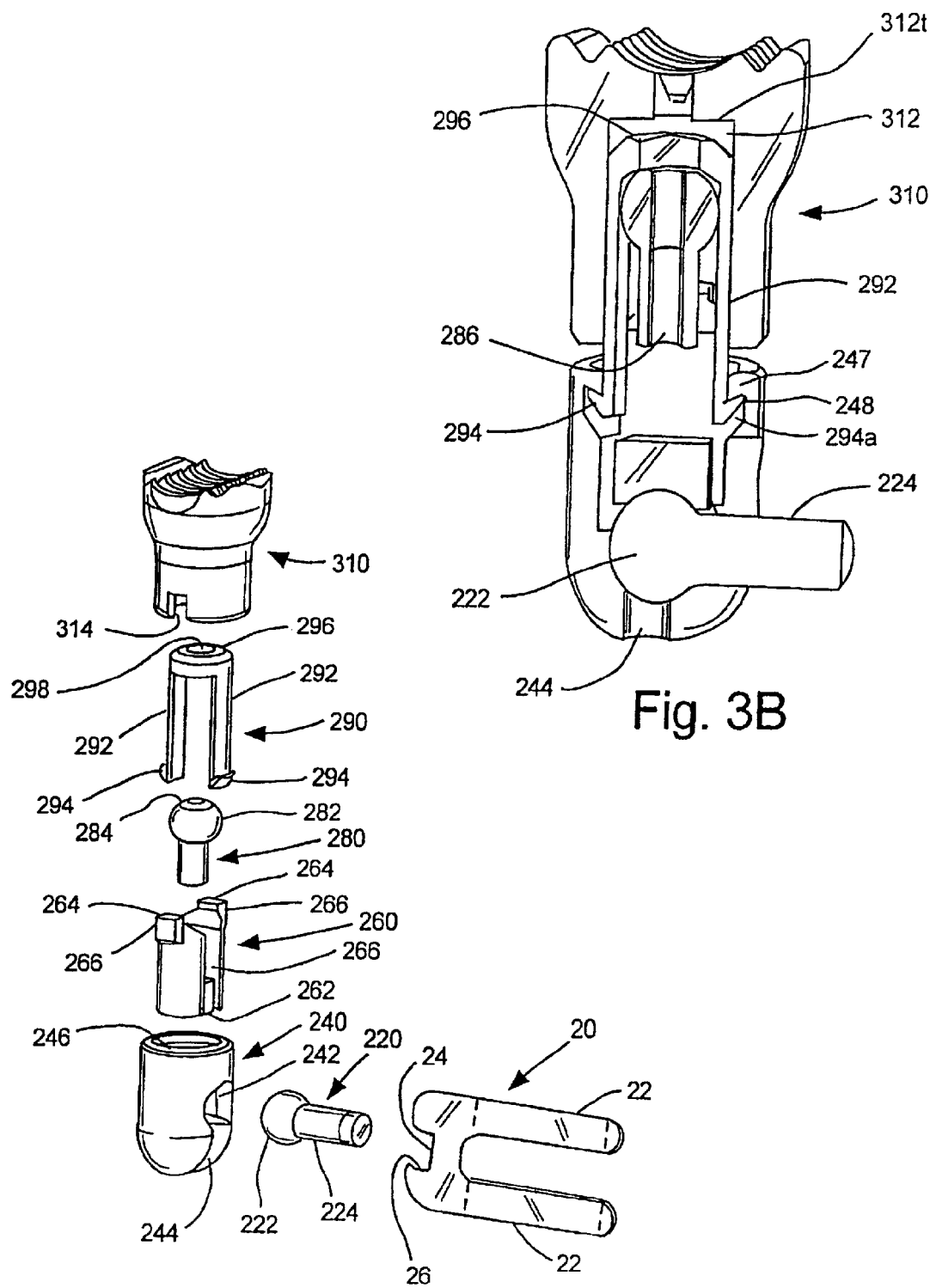
FIG. 3A is an exploded view of the components at the distal end of a stabilizing instrument according to the present invention.
FIG. 3B is an assembled, sectional view of the components shown in FIG. 3B, except for the distal most, foot component.

Referring to FIG. 3A, an exploded view of the components at the distal end of stabilizing instrument 10 are shown which connect the maneuverable arm 30 to the contact member 20. The distal most articulating member 310 of the maneuverable arm 30 includes a cavity 312 (see FIG. 3B) which opens to the distal end of the articulating member 310 and is adapted to at least partially receive coupling members 260, 280 and 290, which are described below. A socket member 240 having an outside diameter of about 0.375 inches in this example, caps the distal end of the stabilizer 10 and is mated to the distal most articulating member 310 via coupling members 260, 280 and 290, in concert with the tensioning cable which runs through the stabilizer.

Socket member 240 includes an opening 242, which is dimensioned to freely receive the ball portion 222 of a connecting element 220 to which contact member 20 is fixed. Socket member 240 further includes a slot 244 dimensioned to receive stem 224 of connecting element 200, allowing it to slide freely in the slot 244 while at the same time preventing ball portion 222 from passing therethrough. A proximal opening 246 is provided in the socket member and dimensioned to receive at least a portion of coupling members 260, 280 and 290.

Coupling member 260 may be a socket cap which is received within the proximal opening. Socket cap 260 includes a base or cap portion 262 dimensioned to abut ball portion 222 and maintain it in its position in the socket member 240. In the example shown, the cap portion has a substantially planar bottom surface with a circular opening dimensioned to ride against the sphericity of the ball portion 222. Of course, other configurations of the bottom surface are contemplated which would accomplish the same function, e.g., the ability to apply force against the ball portion 222 and maintain the ball portion within the socket member 240, while also allowing the ball portion to rotate. Still further, upon increased application of force, the cap portion 262 has the ability to lock the ball portion and prevent it from rotating.

The outer surface of the socket cap 260 is substantially cylindrical and adapted to slidably and rotatably fit within the cavity of the coupling member 240 introduced by the proximal opening 246. This allows rotation of the contact member about the longitudinal axis of the maneuverable arm when the stabilizer is in a non-rigid state. The proximal portion of the socket cap 260 includes driving surfaces 264 adapted to abut against the distal most articulating member 310 and transmit force against the ball portion 222 via cap portion 262 when the cable is tensioned. In the example shown in FIG. 3A, driving surfaces 264 are located on tabs 266 which are dimensioned to be received in slots 314 in the distal most articulating member 310. In this embodiment, upon complete release of tension in the stabilizer 10, the socket member 240 may be pulled in a direction away from the distal most articulating member 310 by a sufficient distance to allow ball portion 222 to be extracted through opening 242, for example to change the setup by replacing the existing contact member 20 with a different one. Thus, a change may be made between contact members to choose a different design or configuration, or even to change to one which operates on a different principle. For example a change from a mechanical contact member, which operates by applying physical pressure against the beating heart tissue, may be replaced with a negative pressure contact member, which engages the heart by vacuum. In this regard, any of the contact members described herein could be exchanged for operation in the stabilizer 10 described. Additionally, other known contact members could be used or adapted to be used by those of ordinary skill in the art. This interchangeability is made possible by the notches 314 which allow separation of the tabs 266 therefrom.

Alternatively, the notches 314 may be replaced by enclosed holes 314' (see FIG. 3C) which maintain the capture of tabs 266 even when the tension is fully relieved in the stabilizer 10. In this case, the socket member 240 cannot be separated from the distal most articulating member 310' and coupling members 260, 280 and 290 by a sufficient distance to remove ball portion 222 through opening 242 (unless a shim within the mount is removed as described below). While this arrangement eliminates the ability to easily interchange contact members, it has the advantage of ensuring that the contact member will not become accidentally disengaged or removed, regardless of the amount of tension (or lack thereof) in the stabilizer 10.

The socket cap 260 further includes recessed or open portions 266 dimensioned to receive the arms 292 of coupling member 290. The recessed portions are continuous over the length of the socket cap 260 and are also defined along the perimeter of the cap portion 262. In this way, the arms 292 interfit with the socket cap and are continuous with the outer perimeter thereof to form a cylindrical surface for rotating against the socket member 240. The interior surface of socket member 240 is undercut near the proximal end to form an annular groove 248 that extends around the interior circumference of the proximal end portion and underlies a lip 248 formed thereby. Upon assembly, tines 294 which extend outwardly from arms 292 at the distal end of the arms, engage the groove 248 and are prevented from being withdrawn from the socket member 240 by lip 247. Because the lip 247 and groove 248 extend around the entire inner circumference of the socket member 240, coupling member 290 is free to rotate with socket cap 260 in an unlocked configuration of the stabilizer 10. The outside ends of the tines 294 are preferably chamfered or beveled 294a to ease the insertion of the coupling member 290 into the socket member 240.

As shown in FIG. 3B, the cavity 312 in member 310 is dimensioned to slidably receive at least the proximal portions of coupling members 260 and 290 with a close fit. Because the tabs 266 engage with either slots 314 or holes 314', the coupling members 260 and 290 do not rotate with respect to member 310, but only with respect to socket member 240. Coupling member 290 is provided with an abutment surface 296 which is adapted to abut against the upper surface 312t that defines the top of cavity 312. A central opening 298 is provided through the abutment surface and proximal end of the coupling member to allow the tensioning cable to pass therethrough.

A cable fitting 280 is provided as a part of the coupling assembly, and includes an enlarged ball-shaped or other shape stop portion 282 which has an abutment surface 284 adapted to abut against coupling member 292 to apply a force thereto when the cable is drawn up thereagainst. Cable fitting 280 also includes a hole or passage 286 passing centrally and longitudinally therethrough, for passage of the cable therethrough.

Each of the coupling components 260, 280 and 290, as well as the socket member 240 and connecting element 220 may be made of a machined biocompatible metal, such as stainless steel, or may be molded, such as by metal injection molding, for example. Alternative metals which are biocompatible and meet the strength requirements for this application may also be employed.

Figures 3C, 4:
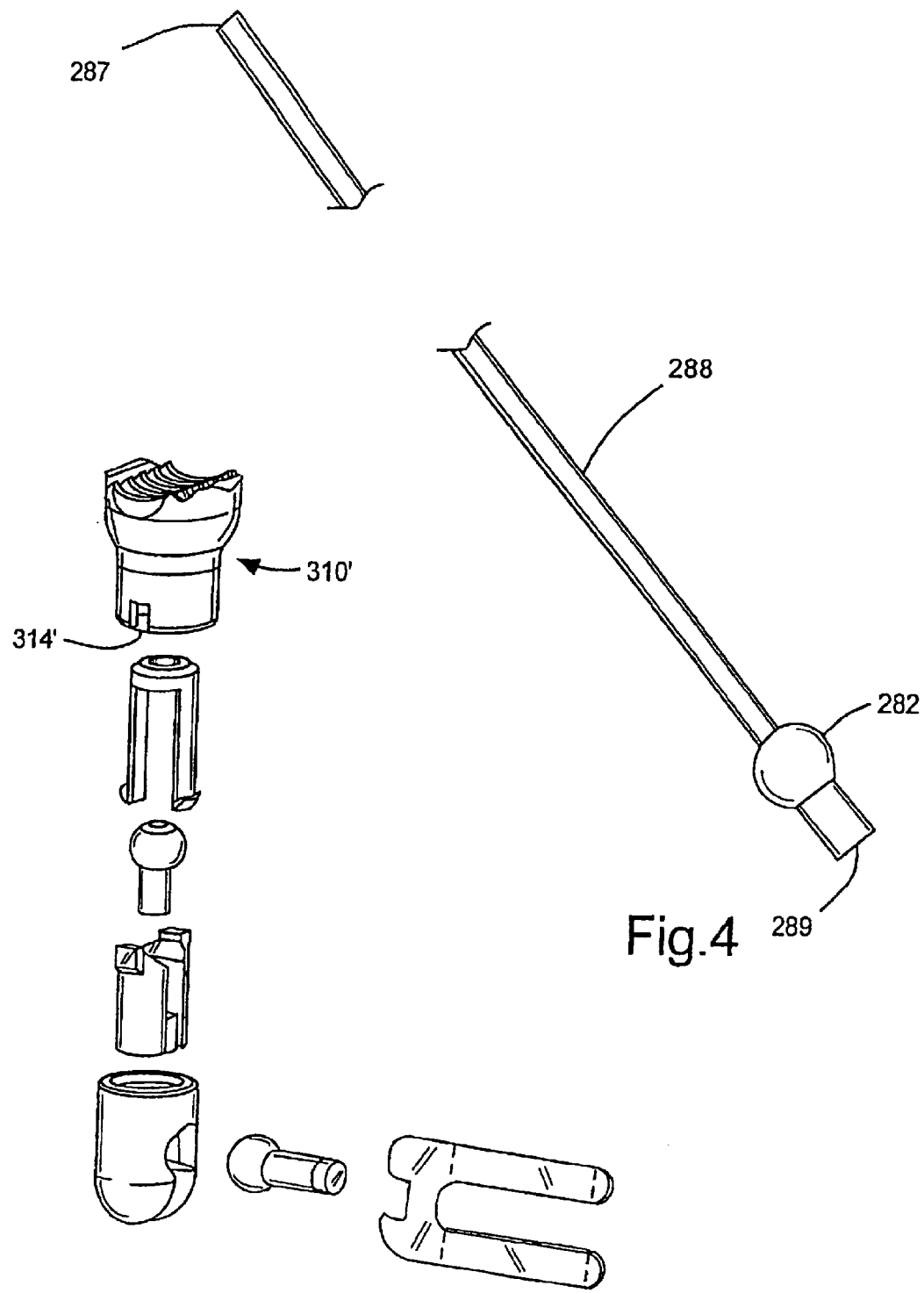
FIG. 3C is an exploded view of the components at the distal end of a stabilizing instrument including a slight variation of that shown in FIG. 3A.
FIG. 4 is a partial plan view of a cable having a cable fitting mounted thereon, according to the present invention.

Referring to FIG. 4, cable 288 is preferably a multi-strand metallic cable made from 300 series stainless steel in a 7×7 configuration (seven strands in each of seven bundles), but may be made of another high strength biocompatible material which would be suitable for such purposes, e.g., Kevlar, titanium and the like. The cable should preferably have a tensile breaking strength of at least about 470 psi. The cable 288 is assembled with the cable fitting 280 by passing the cable 288 through passage 286 and then welding, soldering, swaging, adhering, crimping or otherwise securing the cable fitting 280 to the cable in a manner to withstand tensile forces up to about 470 psi. It should be noted here that 470 psi is a value that is used for the particular embodiment presently being described, and that this value may vary depending upon variation of size or other parameters used in each particular stabilizer device. After fixing the two components together, the distal ends 289 of the components may be made flush by grinding for example. The proximal end 287 is electrocut to length, which, in this example is about twelve inches±a quarter of an inch.

The maneuverable arm 30 comprises a plurality of articulating members or links. Each link includes a hole passing through its center and long its longitudinal axis, to provide a passageway for cable 288 which passes through each link. The links may be made from a high strength, high rigidity plastic such as a rigid glass-filled polyurethane, for example, or other acceptable high rigidity biocompatible plastics known in the art. In another example, the links may be alternately arranged such that links formed of rigid glass-filled polyurethane alternate with links formed of polycarbonate with Teflon and glass fill, for example.

As may be seen in FIG. 1, the links of the maneuverable arm 30 are formed in groups having progressively stepped down outer diameters, where the distal most link 310 has the smallest diameter at its distal end, and the proximal most links have the largest diameters, with intermediate diameters existing between the two ends. This decreasing diameter profile maximizes the amount of free or working space available to the surgeon at the distal or working end of the device, while maintaining additional friction capability toward the proximal end to ensure a sufficient overall rigidity of the device upon tightening the cable.

Figure 4A:
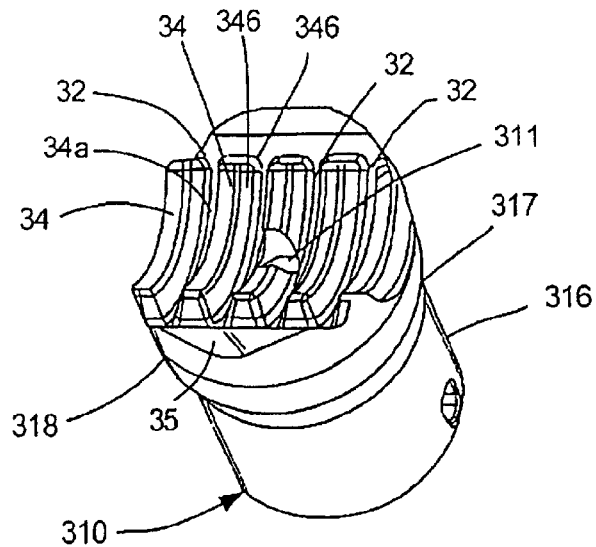
FIG. 4A is a perspective, isolated view of distal most articulating link according to the present invention.
Figure 4B:
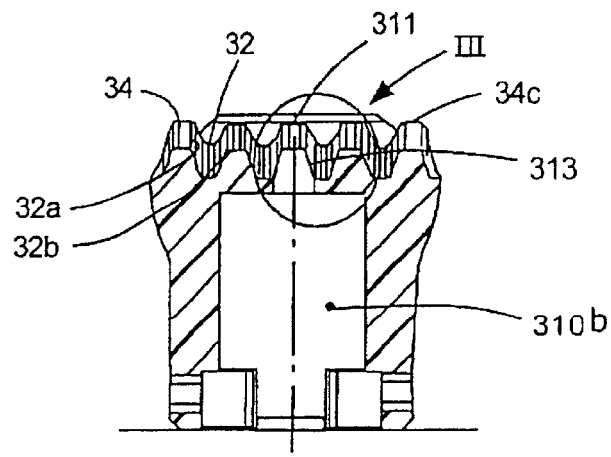
FIG. 4B is a longitudinal sectional view of the link shown in FIG. 4A.

FIG. 4A is a perspective, isolated view of distal most articulating link 310. The distal portion 316 of link 310 has an outside diameter of about 0.400 inches in this example where it forms a rotational joint with socket member 240 such that, in an unfixed state, the socket member 240 is free to rotate about the longitudinal axis 3101 of the link 310. Link 310 includes a central transitional portion 317 that transitions the link to the larger diameter portion 318 at the proximal end thereof. The outer diameter of portion 318 in this example is about 0.500 inches, which is substantially matched to the outside diameter of articulating link 320 with which it articulates.

The articulating joint which is formed between links 310 and 320 is formed by a series of "V-trenches" 32 and teeth 34 aligned parallel across the faces of the links that articulate with one another. In the case of link 310, the articulating face is concave, and the distal articulating face of link 320 that interfaces link 310 is convex. The surfaces are designed to conform to one another, with the V-trenches 32 of link 310 meshing with the teeth (or ridges) 34 of the distal surface of link 320, and the V-trenches 32 of the distal surface of link 320 receiving and meshing with the teeth 34 of link 310. Since both surfaces have the same (although inverse) degree of curvature, they articulate smoothly in the direction of the V-trenches, gliding smoothly in a single plane of rotation only, when the device is in an unrestricted, or untensioned state. Upon the application of forces causing a compression of components 310 and 320 against one another, frictional forces between the teeth and the V-trenches increase making it increasingly difficult to articulate the joining surfaces, until eventually the two pieces become fixed with respect to one another. This fixation can occur at any desired relative positioning between the two links within the range of motion provided by the joint. This is the basis for the ability to fix the device in any desired configuration.

Figure 4C:
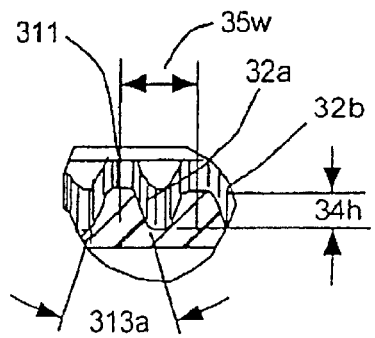
FIG. 4C is an enlarged detailed view of the portion of the link identified by III in FIG. 4B.

Thus, the trenches 32 not only provide a track along which the teeth 34 are guided for rotational articulation of the joint in a plane, but they must have a sufficient aspect ratio and angulation to effect a progressive development of friction as the teeth sink lower into the trenches under compression. Aspect ratio is defined here as a ratio of the depth (or height) of the trench over the average width of the trench. The aspect ratio of the trenches should be at least about 1:2 or greater. Likewise, the aspect ratio of the teeth should also be at least about 1:2 or greater. In the examples shown, the aspect ratio is closer to 1:1. The trenches, for example, may be about 0.055" deep (see FIG. 4C, 34*h*) and about 0.048" average width. The angulation of the each side of the trench with respect to a normal line intersecting the bottom of the trench may be about 10 to 20 degrees and, in the example shown is about 17±1 degrees. Because teeth 34 are angled in a V-shape, in the same way that the V-trenches 32 are configured, as a tooth 34 is forced into a trench 32, the frictional forces increase geometrically due to the increase in width on both sides of the tooth 34*a* and 34*b* that contacts sides of V-trench 32*a* and 32*b* at any given depth. Further, since the arrangement includes a series of parallel aligned V-trenches, any outward give or compliance of a V-trench is counteracted an equal, but opposing force developed in an adjacent V-trench undergoing the same compressive forces against a similarly dimensioned tooth. The V-trench design provides continuously articulating surfaces between the teeth and the trenches and has been found to provide greatly superior frictional results, as compared to existing ball and socket configurations and modified ball and socket configurations, when equal amounts of compressive force are applied to each type of articulating joint design.

In the example shown in FIG. 4A, the link 310 includes four V-trenches 32 alternating with five teeth 34, although it would be known to those of ordinary skill in the art that these numbers could be varied. The peak-to-peak distance 35 between teeth 34 (or valley-to-valley distance between trenches 32) is about 0.100 inches in the example shown (FIG. 4C). the height 34*h* of a tooth 34 (or depth of a valley 32) may be about 0.050 inches and the angle formed by the walls 32*a* and 32*b* of a trench 32 (or by walls 34*a* and 34*b* of a tooth 34) may be about thirty degrees, plus or minus about ten degrees. The width of a tooth, at the top surface 34*c* may be about 0.050 inches. Underlying the opening 311, the link 310 may be tapered to form a conical pathway 313 to enhance the flexibility of the maneuverable arm 30. The conical pathway assists the cable 288 in bending, especially under extreme angles, by providing a pathway which is more curved when a series of these pathways are assembled as in the case of an assembly of links. Angle 313*a* formed by the wall of the pathway 313 may also be about thirty degrees, plus or minus about ten degrees.

In the embodiment shown in FIG. 1, a second link 320 is assembled on the proximal end of the link 320 described above. The links 320 are substantially identical and each have substantially the same outside diameter along the entire length thereof, the outside diameter being about 0.500 inches. The proximal surface of each link 320 is substantially identical to the proximal surface of the link 310. The distal surface of each link 320 has a series of V-trenches 32 and teeth 34 adapted to mesh with a proximal surface of a link 320 or link 310. For the example given, the distal surface has five trenches 32 alternating with four teeth 34, for example, to provide a topography adapted to mate with the five teeth 34 and four trenches of the proximal surface of a link 310 or link 320, for example. Of course, this is merely an example and the configurations may be switched between the two surfaces. Nor is the invention limited to only a 5–4 configuration as more or fewer teeth and trenches may be formed in a series on a surface. The outside diameters of the links may also be different from that described. For example, rather than links having outer diameters of 0.500, 0.600, 0.700 and 0.800 inches, respectively, a smaller maneuverable arm can be made using lengths having outside diameters of 0.400, 0.500, 0.600 and 0.700 inches, respectively. Of course, a larger arm could be produced by scaling up the link sizes, respectively.

Figure 5A:
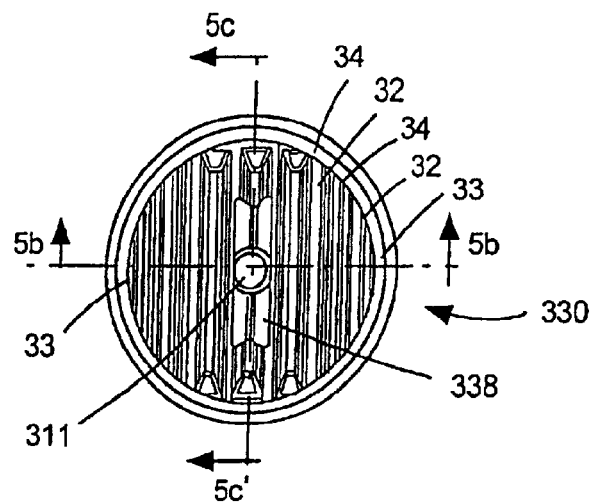
FIG. 5A is an end view of a distal surface of an adapter link according to the present invention.
Figure 5B:
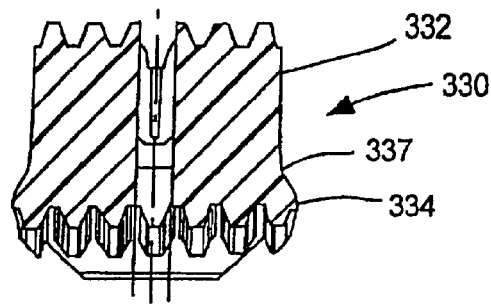
FIG. 5B is a longitudinal sectional view of the adapter link shown in FIG. 5A, taken along line 5B—5B.
Figure 5C:
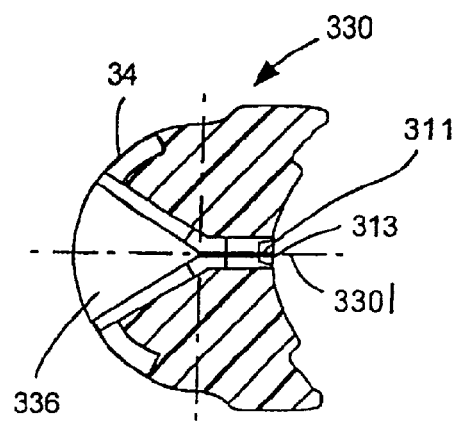
FIG. 5C is a sectional view of the adapter link shown in FIG. 5A, taken along line 5C—5C.
Figure 6:
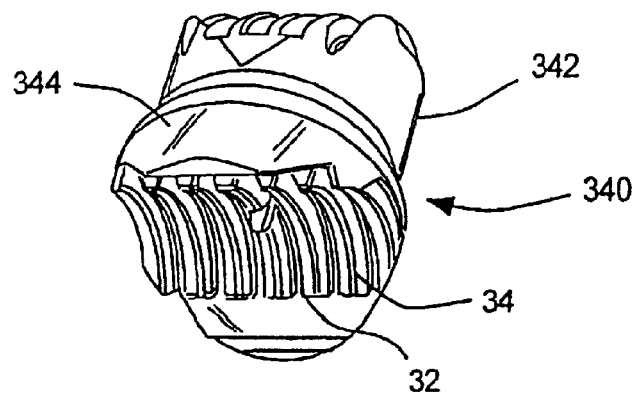
FIG. 6 is a perspective view of an adapter link 340 according to the present invention.
Figure 7A:
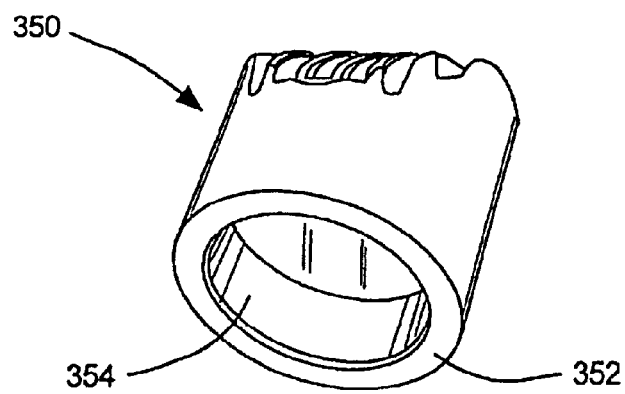
FIG. 7A is a perspective view of a link having a female articulating surface for a rotational joint.
Figure 8A:
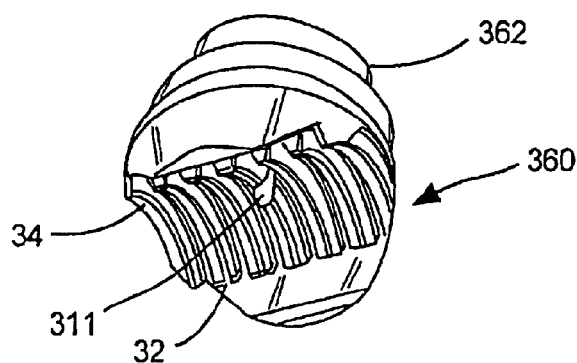
FIG. 8A is a perspective view of a link having a male articulating surface for a rotational joint.
Figure 7B:
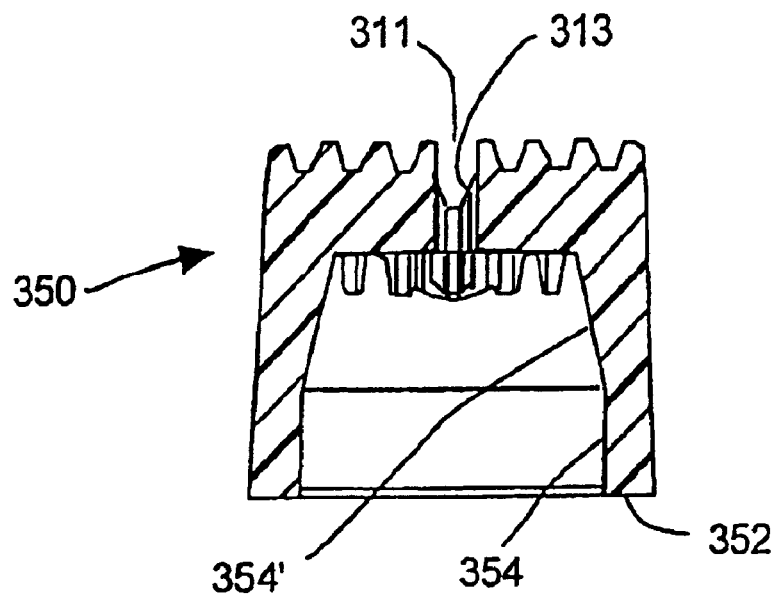
FIG. 7B is a longitudinal sectional view of the link shown in FIG. 7A.
Figure 8B:
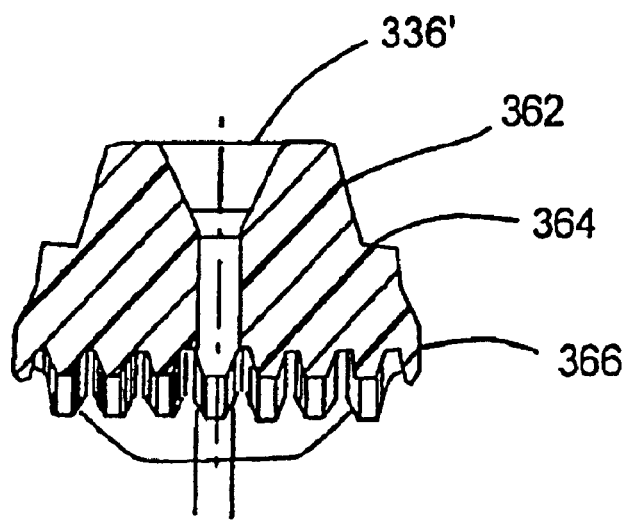
FIG. 8B is a longitudinal sectional view of the link shown in FIG. 8A.

An adapter link 330 is assembled on top of the second link 320 as shown in FIG. 1. Adapter link 330 has a distal portion 332 (see FIG. 5B) which has substantially the same outer diameter as the outer diameter of link 320 (in this example, about 0.500 inches). The distal surface of adapter link 330 is essentially the same as the distal surface of a link 320 as described above, and is shown here in FIG. 5A. Outlying the series of V-trenches 32 and teeth 34 are a pair of side walls 33 which are very similar to teeth 34 but only interface with a trench on one side thereof. Nonetheless the side walls 33 contribute to the balancing of side forces between the trenches and contribute to the articulating function of the joint overall. An angular gap or section 336 is formed in the distal face and central tooth 34 to facilitate the bending of the cable 288 (see FIG. 5C). The angle formed by gap 336 is about sixty degrees plus or minus about five degrees and is centered on the longitudinal axis 3301 of the link 330. The flexibility of each articulating V-trench joint is about fifteen degrees in either direction away from the longitudinal axis 3301.

A transitional portion 337 of the adapter link 330 connects the smaller diameter distal portion 332 to the larger diameter proximal portion 334. In this example, the distal portion has an outside diameter of about 0.600 inches. The distal articulating surface is formed much in the same manner as the distal articulating surfaces of the smaller links described earlier, preferably with the same degree of concavity, although it could be varied. The V-trenches 32 and teeth 34 are also preferably of the same height, width and pitch (i.e., angle of walls) as those described with regard to the smaller links 310 and 320, although the length of these features is necessarily longer so as to span the larger section presented by this surface. Also, since the widths of the trenches and teeth remain the same, a larger number of them are provided in the series on this surface. The function, however, is essentially the same, although a greater amount of friction can be developed when this surface mates with a similarly sized surface, due to the increase total surface area owing to the larger outside diameter surrounding the surface and the increased number (and length) of trenches and teeth meshing with one another. A conical pathway 313 is provided to enhance the flexibility of the maneuverable arm 30. The overall length of adapter link 330, measure from proximal end to distal end is about 0.525 inches in this example.

An additional adapter link 340 may be assembled over adapter link 330 as shown in FIG. 1. Adapter link 340 is constructed essentially the same as adapter link 330, but is scaled larger. That is, the distal portion has an outside diameter of about 0.600 inches and an articulating surface that is convex and adapted to mesh with the proximal articulating surface of the link 330. Again, the V-trenches 32 and teeth 34 are also preferably of the same height, width and pitch (i.e., angle of walls) as all others previously described with regard to the smaller links. The proximal portion 344 has an outside diameter of about 0.700 inches and therefor the length of the trenches and teeth are necessarily longer so as to span the larger section presented by this surface. Also, since the widths of the trenches and teeth remain the same, a larger number of them are provided in the series on this surface. The function, however, is essentially the same, although a greater amount of friction can be developed when this surface mates with a similarly sized surface, due to the increase total surface area owing to the larger outside diameter surrounding the surface and the increased number (and length) of trenches and teeth meshing with one another. A conical pathway 313, though not clearly shown, is provided in the proximal portion to enhance the flexibility of the maneuverable arm, and a gap 336 (not shown) is provided for the same reason. The overall length of adapter link 340, measure from proximal end to distal end is about 0.600 inches in this example.

As mentioned above, the articulating surfaces provide excellent high friction locking surfaces when the links are compressed together, which allows the design of a smaller and lower profile device than has been known previously. Also, since a significantly lower compression force is effective (e.g., a tensioning force on cable 288 of only about four hundred pounds results in a stiffness of the device equally to that requiring a one thousand pound force in some prior art devices), the tightening mechanism can be made smaller, enabling a lower profile of the overall device. Since the V-trench articulating surfaces allow rotation in only one dimension (i.e., rotation in a single plane), at least one rotational joint 355 (FIG. 1) is provided with a plane of rotation normal to the plane of rotation of an adjacent V-trench joint.

Rotational joint 355 is formed between female link 350 and male link 360. By enabling rotation about joint 355, the distal portion of maneuverable arm thus far described may be flexed in any plane of rotation which is coaxial with the longitudinal axis of the rotational joint, since the longitudinal axis also establishes the center of rotation of the rotational joint 355. This greatly enhances the flexibility and versatility of the stabilizer, as to the locations that it can be positioned to address.

Female link 350 is about 0.650 inches long in this example and has an outside diameter of about 0.700 inches. The distal articulating surface is adapted to mesh with and articulate with the proximal surface of the adapter link 340. A central opening 311 is provided in the link 350, the same as all previously described links, and is tapered conically 313 to enhance the flexibility of the cable 288 and maneuverable arm 30 overall. The proximal end of link 350 form a flat annulus 352 which is adapted to interface with a like surface at the distal surface of the male link 360, described below. A opening in the distal end provides a race 354 against which the male portion of the joint articulates during rotation. Race 354 is shown as cylindrical 354 and then conically tapered 354', but may be completely conically tapered.

Male link 360 includes male bearing portion 362 which is adapted to rotate in race 354. The conical tapering of race 354 and the conical taper of male bearing portion 364 allow a finite amount of flexing between the two components such that the rotation joint therebetween will still function without binding or popping out of joint even when the maneuverable arm is maximally flexed. A flat annular surface 364 is provided at the base of the male bearing portion 362 and is adapted to interface with and rotate against annular surface 352, in a relaxed state. Further, the compression of these two annular surfaces together acts to increase the friction resistance between the male and female links, thereby preventing rotation. Additionally, the conical surface of the male bearing portion 362 is force into the race 354,354', thereby frictionally locking the joint. Male link 360 also includes a central opening 311 and conical taper 313 in the proximal portion, as well as about a thirty degree conical taper 336' to enhance the flexibility of the cable 288 and maneuverability of the maneuverable arm 30.

Male link 360 tapers to a larger proximal portion 366 having an outside diameter of about 0.800 inches. The proximal surface is concave with teeth 34 and V-trenches which may be manufactured to the same dimensions (except length) and standards as those previously described.

In the embodiment shown in FIG. 1, four large links 370 are next assembled on the proximal surface of the male link 360, although this number could vary. Since each of the large links is substantially identical, only one will be described here to avoid redundancy. Each large link 370 has a substantially consistent outside diameter over the length thereof, which is about 0.800 inches. The construction is essentially the same as described with regard to links 320, but scaled up to size. Therefor, each link 370 provides substantially more surface area against which the surfaces articulate, as well as develop friction under compression. In this way, the large links develop a great deal of rigidity and fixing strength when the cable is tensioned.

A large diameter female link 380 interfaces the fourth large link 370. Female link 380 is constructed essentially the same as female link 350, but is scaled up to a size having about a 0.800 inch outside diameter. The distal end includes V-trenches 32 and teeth 34 which mate with the corresponding V-trenches and teeth in the proximal end surface of link 370. The distal end includes a flat annular surface and a race which are formed the same as 352 and 354, only of slightly larger dimension. Large female link 380 forms a second rotational joint 385 with the distal portion of mount 40.

Figure 9A:
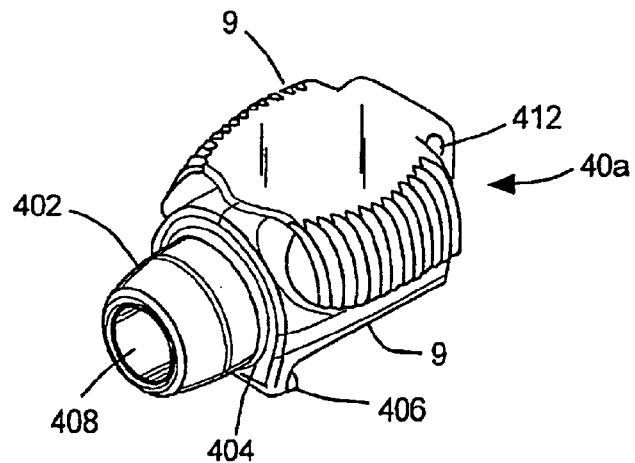
FIG. 9A is a perspective view of a distal portion of a stabilizer mount according to the present invention.
Figure 9B:
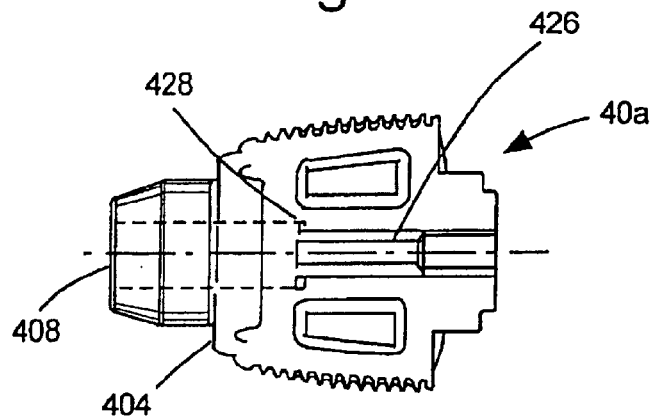
FIG. 9B is a bottom view of the distal portion shown in FIG. 9A.
Figure 9C:
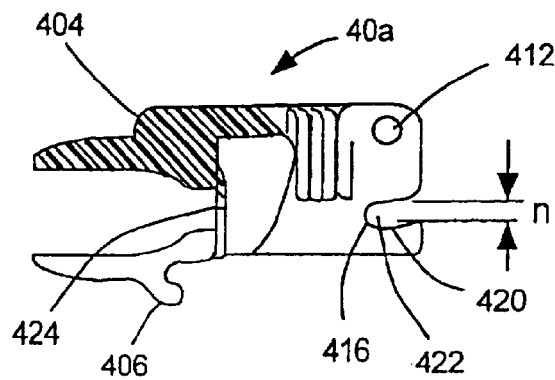
FIG. 9C is a longitudinal sectional view of the distal portion shown in FIG. 9A.

FIG. 9A is a perspective view of the distal portion 40a of mount 40. The distal end of distal portion 40a extends a male bearing portion 402 male bearing portion which is adapted to rotate in the race of the large diameter female link 380, or, is actually the case when mount 40 is fixed to a stationary object such as a retractor, to allow the race of the large diameter female link 380 to rotate on the male bearing portion 402. The conical tapering of the race and the conical taper of male bearing portion 402 allow a finite amount of flexing between the two components such that the rotation joint therebetween will still function without binding or popping out of joint even when the maneuverable arm is maximally flexed. A flat annular surface 404 is provided at the base of the male bearing portion 402 and is adapted to interface with and facilitate rotation of the annular surface of the large female link 380, in a relaxed state. Further, the compression of these two annular surfaces together acts to increase the friction resistance between the male and female links, thereby preventing rotation. Additionally, the conical surface of the male bearing portion 402 is forced into the race of the large female link 380 upon tightening of the device, thereby frictionally locking the joint.

The second rotational joint 385 is provided with a plane of rotation normal to the longitudinal axis of the distal portion 40a. By enabling rotation about joint 385, the entire maneuverable arm 30 may be flexed in any plane of rotation which is coaxial with the longitudinal axis of the rotational joint, which is also the longitudinal axis of the distal portion 40a, since the longitudinal axis also establishes the center of rotation of the rotational joint 385. Further, the portion of the maneuverable arm 30 that is distal to rotational joint 355 may be flexed in a plane of rotation which is coaxial with the longitudinal axis, but different from the plane of flexation of the portion of the maneuverable arm that is proximal to the rotational joint 355. This, of course, is made possible by the rotation of rotational joint 355. Thus, even greater flexibility and maneuverability of the stabilizer is achieved by the provision of two rotational joints. It must be noted here that the present invention is not limited to two rotational joints, as more may be used (or fewer).

Mount 40 may be molded of a high strength and highly rigid composite polymeric material such as polycarbonate with Teflon and glass fill, for example having about 10 percent Teflon, and 20 percent glass fiber fill, with the percentages being weight percentages. Alternatively, other materials such as CCP, polyurethane, etc. could be employed for this purpose. As an alternative to molding, it would also be possible to machine these components. Because of the simplicity of the design of mount 40, it can be made to be extremely low profile, thereby taking up less space at the location of mounting, and more importantly, positioning the entire stabilizer very close to the stationary mounting site and minimizing the amount of space that it extends into the surgical site.

An important function of mount 40 is to securely fix stabilizer 10 to a relatively immobile object, such as a sternal retractor, so as to maintain the stabilizer in a fixed position relative to the beating heart. The stabilizer itself can be made rigid through the mechanisms described herein, and could possibly be hand operated, but the stabilization process is more effective and requires fewer hands in the vicinity of the surgical site if the stabilizer can be anchored to an immovable object. Mount 40 is adapted to be clamped to an appropriate rail, such as on a sternal retractor, for example, and secured by rail grips 406 and 410. Distal and proximal portions 40a and 40b are joined by a hinge formed by passing a hinge pin (not shown) through hinge pin receptacles 412 and 414. The hinge pin is a straight metallic shaft which is press fit into the pin receptacles. The hinge pin is preferably formed of medical grade stainless steel or an alternative biocompatible metal. The hinge joint allows the portions 40a and 40b to be pivoted toward and away from one another about the hinge pin. When the portions 40a and 40b are pivoted away from one another, rail grips 406 and 410 also move away from one another. This position is used for releasing the mount from a rail and for positioning the mount over the rail prior to engaging the mount to it.

Distal portion 40a has a living hinge 416, located directly beneath hinge receptacle 412, which is adapted to receive and engage a second hinge pin 418 mounted in proximal portion 40b beneath hinge receptacles 414. The neck 420 of living hinge 416 defines a slot having a dimension slightly smaller than the outside diameter of second hinge pin 418. As proximal portion 40b is approximated with distal portion 40a, second hinge pin 418 contacts the sides of neck 420, thereby exercising living hinge 416 by forcing neck 420 open to allow second hinge pin 418 to pass by and engage in hinge receptacle 422. Hinge receptacle 422 is dimensioned slightly larger than the outside diameter of second hinge pin 418. Second hinge pin 418 seats in hinge receptacle 422, thereby allowing living hinge 416 to relax and neck 420 to return to its original dimension and locking hinge pin 418 in. This entire operation resembles a "snap fit" and securely fixes the portions 40a and 40b in approximation with one another. At the same time, rail grips 406 and 410 are brought into a fixed configuration, gripping both sides of the rail on which the mount 40 is secured. The release operation is just as simple, where the mount portions can be simply "snapped" open and pivoted away from one another to dismount the stabilizer 10 from a rail. The fixed position of the mount 40 may be designed to completely secure the stabilizer 10 to a rail, or it may be designed to clamp the rail snugly, thereby stabilizing the device 10, while still allowing the mount to be slid along the rail (under a significant amount of friction) to reposition it.

Mount 40 is provided with a large opening 408 which funnels down to a smaller passageway 424 through which cable 288 is passed through upon assembly of the maneuverable arm 30.

Assembly of the Stabilizer

After securely fixing cable fitting 280 to cable 288 and finishing the ends of the cable 288 as described above, coupling member 290 is assembled over cable 288 by threading it over the proximal, or free end of the cable and sliding it to the end fixed to the cable fitting 280 to abut stop portion 282. Socket cap 260 is then placed over the distal end of the cable fitting 280 and interfit with coupling member 290, thereby surrounding stop portion 282 together with arms 292. Socket member 240 is then snap fit over the coupling assembly, thereby engaging tines 294 with lip 247, after which links can begin to be added.

The distal most link 310 is assembled over the proximal end of the cable and slid down to engage driving surfaces 264 of socket cap 260. If the link 310 has notches 314, the driving surfaces 264 simply engage notches 314 and must be maintained pressed into position or they may fall out of position if no compression is maintained. If the link 310' has holes 314', then the driving surfaces may snap into position and be secured there.

The remainder of the links, 320, 330, 340, 350, 360, 370 and 380 are then assembled in order by simply sliding them from the proximal end of the cable down into position over one another and oriented so that the V-trenches and teeth engage with one another on interfacing surfaces. A safety crimp is then formed over the cable 288 proximally of the large female link 380. The safety crimp is formed by placing a small tubular piece of ductile metal over the cable and then crimping or deforming the ductile metal so that it is anchored in a desired position on the cable. The deformed metal is too large to pass through the central opening in the large female link 380 and thus serves as a precautionary measure to maintain all of the links on the cable, should there be a failure in the vicinity of the mount or proximal to the mount.

The maneuverable arm 30 now having been loosely preliminarily assembled, the proximal end of cable 288 is passed through large opening 408 in distal portion 40a of mount 40 and through opening 424 whereby distal portion 40a is positioned loosely up against large female link 380. An open channel 426 is provided in the underside of distal portion 40a proximally of opening 424, which allows access to cable 288. An additional cable fitting (not shown), similar to the safety crimp, but longer to increase the amount of friction, is slid over the proximal end of cable 288 and positioned adjacent opening 424 where it is securely crimped.

Figure 10A:
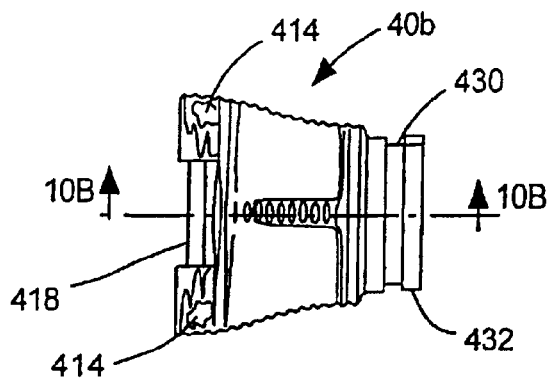
FIG. 10A is a plan view of a proximal portion of a stabilizer mount according to the present invention.
Figure 10B:
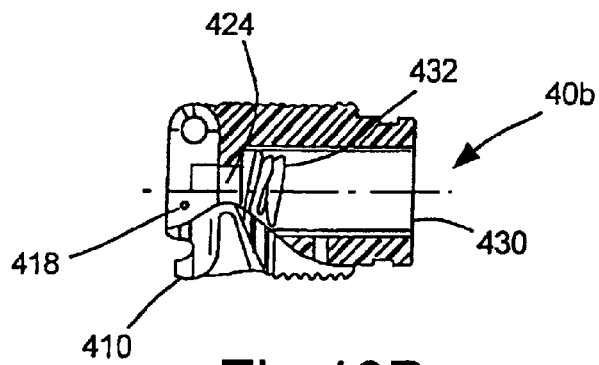
FIG. 10B is a longitudinal sectional view of the proximal portion shown in FIG. 10A, taken along line 10B—10B.
Figure 10C:
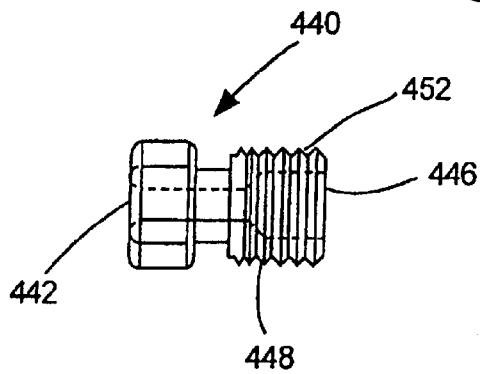
FIG. 10C is a plan view of a screw member according to the present invention.
Figure 10D:
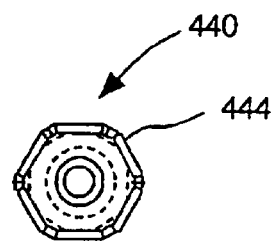
FIG. 10D is an end view of the screw member shown in FIG. 10C as viewed from the left in FIG. 10C

The second hinge pin having been secured into place in the proximal portion 40b, the proximal portion 40b is then assembled with the distal portion 40a, after passing the cable through the central opening of proximal portion. Assembly of the mount portions is made by aligning hinge receptacles 412 and 414, and press fitting the first hinge pin therein. A biasing member 432, such as a coil spring for example, and screw 440 are next inserted into the proximal opening 430 of proximal portion 40b at the same time passing cable 288 through the central opening of the biasing member and central opening 442 that passes through screw 440. Screw 440 is inserted head first, and opening 430 is configured so as to prevent rotation of the screw 440 with respect to the mount 40 once the screw 440 has been inserted. For example, the version shown in FIG. 10D has a hexagonal head 444 and opening 430 has a hexagonal cross section which allows the head 444 to be slid into opening 430, but prevents head 444 from rotating once it has been slid into opening 430. The shape of the head 444 and 430 may be varied, as would be apparent to those of ordinary skill in the art, so long as the opening allows the head to be slid in and then prevents rotation of the head once in position. Biasing member 432 ensures that the proximal portion of the screw 440 and the threads 452 surrounding it are maintained in a position that extends from mount portion 40b to ensured that a torque member (described below) can be positively threaded thereto, in a repeatable and reliable fashion.

Figure 10E:
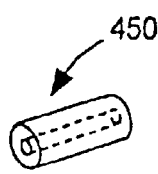
FIG. 10E is a plan view of an anchor according to the present invention.

An enlarged opening 446 is provided in the proximal end of the screw 440 which is dimensioned to receive an anchor 450 (FIG. 10E) that is slid over the cable 288 and crimped into place to secure the screw 440 in position and to further lock the assembly. Opening 446 tapers to join opening 442 and thereby forms an abutment surface 448 against which the anchor 450 is secured. Anchor 450 is preferably formed of a malleable metal such as brass or aluminum, for example, and screw 440 is preferably metal, such as metal injection molded 316 series stainless steel, for example. Threads 452 may be lubricated with a grease having a vegetable oil, silicone or other biocompatible base, to smooth the tightening operation, described below.

Figure 10F:
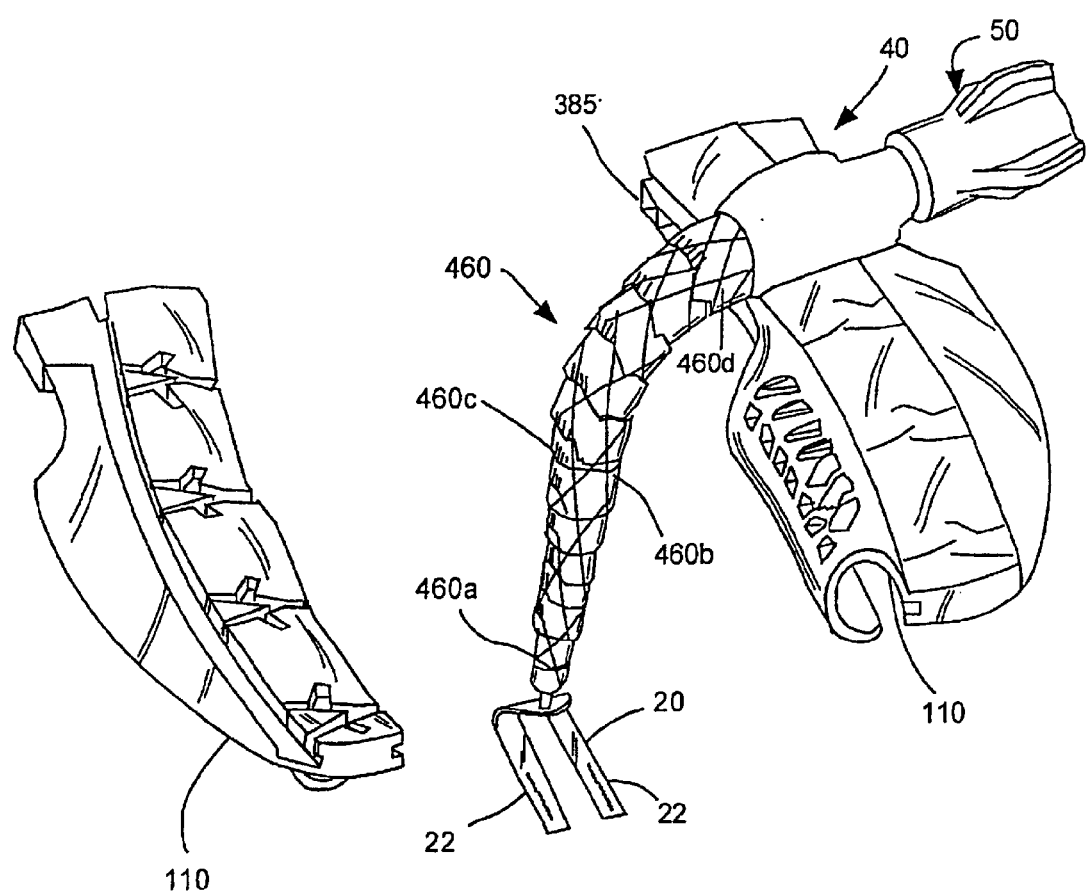
FIG. 10F is a perspective view of a stabilizer device including an optional flexible sleeve according to the present invention.
Figure 11:
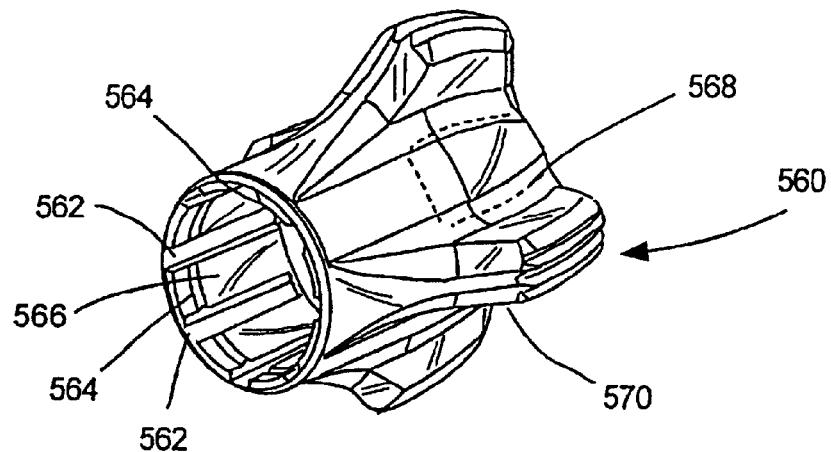
FIG. 11 is a perspective view of a knob according to the present invention.

Optionally, a flexible sleeve 460 may be positioned over the links of the maneuverable arm 330, as shown in FIG. 10F, if desired. The sleeve may, although does not necessarily need to, be formed in two parts such that a distal part is slid over the distal portion of the arm 330 where it is attached to the distal most articulating member at 460a and at the distal portion of the intermediate rotational joint at 460b. Similarly, the proximal part of the sleeve 460 is fitted over the proximal portion of the arm 330 where it is attached to the proximal portion of the intermediate rotational joint at 460c and at the distal portion of the rotational joint at the proximal end of arm 330 at 460d.

Although the sleeve could be formed of an elastomer such as silicone or dip molded PVC, for example, it has been found that the flexibility of the links about an axis perpendicular to the longitudinal axis of the maneuverable arm 330 may be limited by such a sleeve, although rotation about the longitudinal axis is not so limited. It has been found that superior results may be achieved by using a material that has more axes of elasticity, such as a knitted LYCRA® or SPANDEX material having a four or six way stretch. Such a sleeve 460 does not preload the maneuverable arm significantly so as to restrict its flexibility in either of the motions discussed above. Any of the sleeve materials serves the function of further ensuring that no foreign materials (e.g., sutures, surgeon's gloves, etc.) will be trapped or snagged in any of the articulating joints of the maneuverable arm 330. An additional advantage of a sleeve 460 is that it provides an extra degree of integrity to the maneuverable arm 330, helping maintain each of the links in its intended position. Further, if there should be a failure in the cable 288 or other factor causing disintegration of the device, the sleeve 460 would prevent loss of links and maintain the integrity of the device.

After anchoring the screw 440 as described above, there is still a sufficient amount of slack in the assembly to allow the socket member 240 to be separated from distal most link 310, thereby freeing the space defined by opening 242. This allows ball 222 to be inserted into the socket member 240 through opening 242. After insertion of the ball, a stop or shim is placed into slot 428, thereby taking up some of the slack in cable 288 and preventing a separation of socket member 240 from the assembly by a sufficient distance to remove ball 222. This is an optional step which may be skipped if it is desired to interchange members 20 after complete assembly of the stabilizer.

Assembly of the tensioning mechanism 50 continues by insertion of torque member 520 into knob 560. The torque member 520 is preferably formed of a hard polymer material such as polycarbonate. Torque member 520 is threaded internally with threads 522 dimensioned to mate with the external threads 452 on the shaft of screw 440. Threads 522 and 452 must be strong enough to withstand the tensile forces that are applied to cable 288 when they are threaded together. The threads must therefor be strong enough to withstand tensile forces of at least 470 psi in the example described above.

Figure 12A:
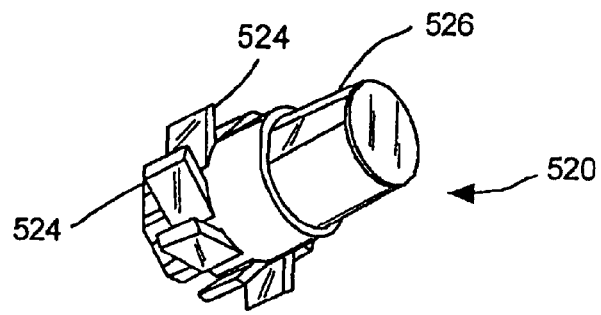
FIG. 12A is a perspective view of a torque member according to the present invention.

Torque member 520 further includes a torque limiter formed by fins 524. Fins 524 are integrally molded of polycarbonate with torque member 520, and are placed so as to engage trenches 562 in knob 560 when torque member 520 is slid into knob 520. Fins 524 are angled with respect to the body of torque member 520 in a clockwise direction when viewed from the proximal end of torque member 520, as shown in FIG. 12A.

Knob 560 includes tabs 564 which extend from ribs 566 that separate the trenches 562. Tabs 564 are configured to lock into circumferential annular trench 430 on the proximal portion of proximal mount portion 40b in a snap fit manner. That is, the inner diameter of a circle formed by connecting the tops of tabs 564 is smaller than the outer diameter of the proximal end 432 of mount portion 40b. Thus, when the knob 560 is pushed over the proximal end 432, tabs 564 deflect or give somewhat to pass by the proximal end and snap into place in circumferential trench 430, which has an outside diameter slightly smaller than the inside diameter formed by tabs 564.

Knob 560 has an internal cup or cylinder 568 extending from the center of the proximal end inside of knob 560. Cup 568 is a hollow cylinder dimensioned to receive a spacer 526 that makes up the proximal end portion of torque member 520. Spacer 526 maintains threads 522 in alignment with threads 452 on screw 440 when knob 560 is snapped onto the mount 40. Threads 522 are self starting and will engage threads 452 when knob 560 is turned in a clockwise direction. When knob 560 is turned a sufficient amount in the counterclockwise direction, threads 522 disengage from threads 452 to ensure that no residual tension is left on cable 288 so that the maximum flexibility of maneuverable arm 30 is available. By receiving and closely holding spacer 526, cup 568 maintains threads 522 in alignment with threads 452 to ensure that torque member 520 does not become cross threaded when knob 560 is turned clockwise.

Knob 560 includes four extensions 570 radially extending from equally circumferentially spaced locations on the proximal portion of knob 560. The present invention is not limited to the use of four extensions, as more or fewer extensions may be used and still achieve the desired results. Extensions 570 not only provide a convenient non-slip handle to be grasped by the hand of an operator, but also provide additional mechanical advantage to apply torque for tensioning cable 288. As noted above, because of the efficiency of the frictional surfaces provided by the V-trench and tooth design on the articulating links, less force is needed to sufficiently rigidity the stabilizer than that required by prior art designs. Because of this, less mechanical advantage need be provided by extensions 570 compared to those in the prior art, therefor they can be made to extend by a significantly smaller distance. This is important because it allows the entire device 10, and particularly the mount 40 to be made to assume an extremely low profile and thereby provide the surgeon with more working space. Knob 560 may be made from the same materials as the links.

Operation of the Stabilizer

After snapping knob 560 into position on the proximal portion 40b of mount 40, the stabilizer is fully assembled. A position on a rail of a sternal retractor is chosen where the stabilizer is to be mounted. The stabilizer 10 is then mounted to the rail in the desired location in the manner described above. Alternatively, as also noted above, the mount can be snapped together for a hand held use (or clamping by other means) of the stabilizer 10, and all of the following steps would apply to each use. After closing the mount 40 and while the stabilizer is still in a fully relaxed, flexible state, the surgeon then manipulates maneuverable arm 30 and heart contact member 20 to assume a configuration best suited for approximation of the heart tissue that is desired to be stabilized. Manipulation can include flexing any combination or all of the links at the V-trench articulations, as well as rotation about either or both of the rotational joints. Additionally, heart contact member is freely rotatable 360 degrees about the longitudinal axis of the device 10, as well as nearly 180 degrees in a plane coaxial with the longitudinal axis of the device. This effectively gives the surgeon three degrees of freedom about which to position heart contact member 20.

The surgeon may desire to do a "coarse" positioning of the stabilizer 10 to approximate a configuration deemed best for contacting the target tissue and then apply some tension to cable 288 by torquing knob 560 an amount enough to increase friction between the links (as well as between the ball of heart contact member and coupling members) so that the stabilizer holds the configuration under its own weight, but not enough to make the configuration rigid. The surgeon can then make fine adjustments to the configuration at particular joints or locations along the stabilizer, without concern for displacing the semi-fixed configurations of those joints that do not need to be adjusted. After fine adjustment has been completed, knob 560 is torqued to the fully rigidity the stabilizer 10.

As knob 560 is torqued in a clockwise direction, threads 522 and 452 engage to draw screw 440 in a proximal direction with respect to stabilizer 10. Torque member 520 is stopped from movement in the distal direction when its distal surface abuts against the proximal surface of proximal portion 40b of mount 40. Since screw 440 is securely fixed to cable 288, it draws cable 288 in the proximal direction as it moves, thereby placing the cable under tension. This draws stop member 282 against coupling member 290 which is also drawn in the proximal direction and tines 294 at the same time draw socket member 240 in the proximal direction. Abutment of the distal most link 310 against driving surfaces 264 maintains socket cap 260 stationary relative to the movement of socket member 240, which causes a compression of ball 222, thereby fixing heart contact member 20.

Compression occurs between distal most link 310, by the force applied through driving surfaces 264, and mount 40, by the force applied through torque member 520 as cable 288 is brought under tension, which locks every articulated joint in its assumed configuration. Stabilizer 10 then functions as a rigid member to provide the desired stabilizing surface against which the target tissue is maintained relatively motionless during the surgical procedure.

Figure 12B:
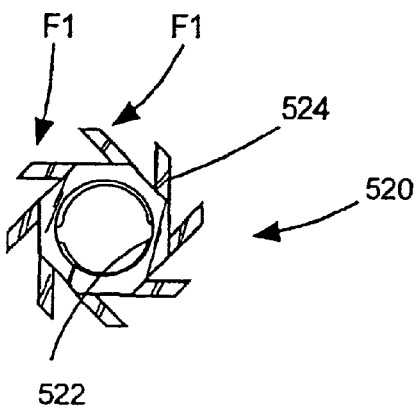
FIG. 12B is an end view of the torque member shown in FIG. 12A as viewed from the left in FIG. 12A.

Fins 524 are designed to act as a torque limiter or clutch during tensioning of cable 288. As knob 560 is rotated clockwise, trenches 562 engage fins 524 to drive them in a direction shown by force $F_1$ in FIG. 12B. When the torque required to further tension cable 288 reaches a predetermined limit (i.e., the torque required to generate a tension of about 400 psi in this example), the force exerted by trenches 562 against fins 524 is deflects the fins by an amount sufficient to allow them to escape from within the trenches. At this level, continued torquing of the knob 560 in the clockwise direction will only result in a clicking sound as the fins 524 continually engage and escape from successive trenches, while torque member 520 remains stationary relative to knob 560. This design ensures that the device can be used consistently, with essentially the same amount of tension applied to the device with each use, rendering its performance more predictable. It prevents over-tightening as well as under-tightening, thereby greatly reducing the risk of cable failure (over-tightening) or lack of rigidity in the stabilizer (under-tightening). Furthermore, this design compensates for the differences in arm strength of the users operating it, and it gives audible feedback as to when the device has been optimally tensioned.

The Heart Contact Members

The heart contact member 20 shown in FIG. 1 is designed to improve the visibility to the surgeon, that is to increase the areas of the heart which is visible to the surgeon during the procedure, while still providing the necessary suppression of heart movement to enable the efficient construction of the anastomosis. More particularly, in this embodiment, a pair of contact members 22 extend from a common base portion 24 which bends away from a general plane in which the contact members 22 lie, where it is connected to stem or post 224, which connects ball 220 to the heart contact member 20 for connection with the rest of the stabilizer 10 as discussed above. The oblique angle between contact members 22 and common base portion 24 provides the ability to extend the contact members 22 away from the maneuverable arm 30 and insure that the arm 30 and common base portion 24 do not obstruct the surgeon's view.

Common base portion 24 includes a slot 26 into which post 224 is fitted for connection thereto. Post 224 may also be provided with a slot 226 which captures a portion of common base portion at the same time that slot 26 borders along the length of post 224. This provides a fairly secure mechanical fit which is fully reinforced by welding the two components together. Alternatively, the two pieces could be manufactured as a single component by metal injection molding. Ball portion 222 may also be fixed to post 224 by welding, or could also be manufactured integrally by metal injection molding. Ball 222 is made larger than previously used in prior art devices to provide a larger frictional area upon which to lock the ball joint that ball portion 222 forms a part of and also to enhance the smooth operation of the joint. Because the socket member 240 of the ball joint arrangement is free to rotate about the longitudinal axis of the stabilizer 10, it is possible to design the socket member to have only one opening 242 and still achieve an even greater flexibility in positioning heart contact member 20 than prior art devices having a non-rotatable socket member that have four openings circumferentially spaced about the socket member. Also, the socket member has greater strength due to this design and can withstand the forces applied by a larger ball.

Figure 13A:
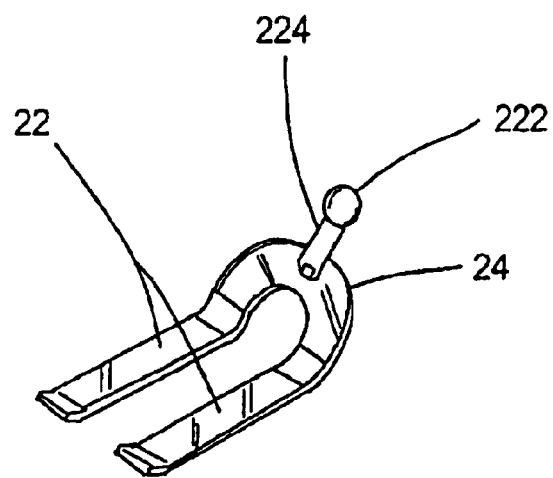
FIG. 13A is an example of a tissue contact member according to the present invention.
Figure 13B:
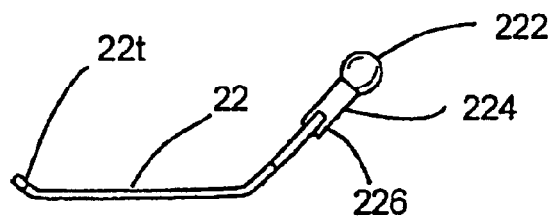
FIG. 13B is a side view of the tissue contact member shown in FIG. 13A
Figure 13C:
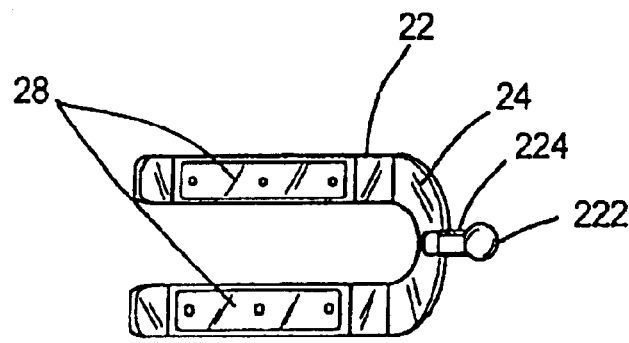
FIG. 13C is a bottom view of the tissue contact member shown in FIG. 13A.

Contact members 22 may have frictional surfaces 28 on the underside thereof (FIG. 13C) to more securely engage the tissue that they contact. The tips 22t of the contact members 22 may be bent upward in the forms of "ski tips" to prevent edge effects (e.g., stress concentration, cutting, chafing, etc.) against the tissue which might otherwise be caused by straight tips. The shape of contact members 22 may be varied depending on the clinical assessment by the surgeon, or by the design of other instruments used to complete the anastomosis, for example.

The contact members may also be modified to include apertures, openings or attachments to facilitate connection with sutures or other devices used to achieve the stabilization and/or anastomosis. Examples of alternative heart contact members that may also be modified for use with the present stabilizer can be found, for example, in U.S. Pat. No. 6,036,641 and in copending U.S. application Ser. No. 09/305,811, filed May 4, 1999, entitled "Surgical Retractor Platform Blade Apparatus", the disclosures of both of which are herein incorporated by reference in their entireties.

Additional varieties of heart contact members may also be provided for connection to a stabilizer 10 according to the present invention. Referring to FIGS. 14A–14D, an example of a heart contact member 600 is shown which uses negative pressure to facilitate engagement of the surface of the heart. Heart contact member 600 includes a pair of contact members 602 which typically engage the surface of the heart on opposite sides of a coronary artery. Heart contact member is typically positioned such that the coronary artery or other anastomosis site runs lengthwise in the space between the contact members 602.

For beating heart procedures where the target vessel is occluded, heart contact member 600 preferably has a construction that does not occlude or otherwise contact the vessel as contact members 602 are placed on opposite sides of the coronary vessel portion to be stabilized. Thus, contact members 602 are spaced apart at a distance such that a coronary artery can be positioned therebetween. Although the configurations of the tissue stabilizers herein are shown to include two contact members, it is noted that a functional, although less effective tissue stabilizer could be formed according to the principles described herein using only one tissue contact member. Of course, more than two tissue contact members could also be configured. This is true not only of the example shown in FIGS. 14A–14D, but of all tissue contact members contemplated for use in the present invention.

When the heart contact member is configured to facilitate the use of negative pressure to engage the surface of the heart, such as with heart contact member 600, contact members 602 may each be provided with a thin, compliant seal 604 which is preferably molded into the contact member. Seal 604 is very compliant and flexible, with a Shore hardness of about 50, for example, and tapers similar to a "knife edge", so that it conforms easily to the topology of the tissue that it contacts when a vacuum is drawn through the contact member 602, thereby providing an effective seal between the heart contact member 600 and the tissue. Seal 604 is preferably molded from a soft and compliant elastomer such as a thermoplastic urethane, e.g. Softflex 0615, available from Network Polymers, Inc. Optionally, the distance that the seal extends from the contact member 602 may vary such that it extends by a relatively greater distance near the tip or distal end of the contact member 602 to provide a variable seal (as shown in phantom by reference numeral 604' in FIG. 14B). The variable seal configuration may help to ensure that a seal is maintained at the distal end of the contact member 604 and that a vacuum pathway is also maintained, as the cross sectional area and thus volume of the distal end is reduced.

Contact members 602 are connected to manifold base 606 over integrally molded fittings 608 extending therefrom. The fittings 608 each include an enlarged circumferential lip 610 over which the contact members 602 are dimensioned to be snap fitted, so that there is only about 0.0005" tolerance per side of the fit between the parts an therefor no O-ring or other seal is required to seal the connection. Each contact member has a circumferential trench into which the respective lip fits. This results in a more rigid connection between each contact member 602 and the manifold base 606 making the heart contact member 600 more rigid overall, thus resulting in an improved stabilizer device. Additionally, the contact members 602 retain the ability to rotate with respect to the manifold 606.

Connecting element 200 is fixed to the manifold 606 opposite fittings 608 and is preferably fixed by molding, adhesives or other equivalent. A third fitting 608 having a similar configuration to those fittings that engage the contact members 602, extends from an end of the manifold 606. A rotatable fitting 612 is internally dimensioned to be snap fitted over the third fitting 608 and to be rotatable with respect to the fitting after mounting. Rotatable fitting 612 has an inner circumferential trench dimensioned to tightly receive lip 610 so that no O-ring is necessary. An end cap 614 is ultrasonically welded to the rotatable fitting 612 to complete the seal with the manifold 606. Rotatable fitting allows greater freedom in positioning the heart contact member 600 with less resistance from the line connecting the vacuum source thereto. For example, the contact members 602 and manifold 606 can be rotated while maintaining a constant position of the rotatable joint 612 and the vacuum line connected to it.

An inlet tube 616 having an inlet opening 618 is provided to fluidly connect a vacuum line with a hollow space or chamber defined within manifold base 606 and rotatable fitting 612. The internal chamber within manifold base 606 and the fittings 608 extending therefrom provide for convenient distribution of a single vacuum source connected by vacuum line to inlet tube 616 to multiple contact members 602. Inlet tube 616 may have one or more barbs 620 to facilitate the secure and leak-free attachment of a length of flexible tubing (not shown) coming from a vacuum pump or other vacuum source (not shown) as is commonly known in the art. In an alternative embodiment, inlet tube 616 may be replaced with a fitting similar to 608 and a vacuum line can be provided with a fitting similar to the interior fitting of rotatable fitting 612 so as to provide a rotational joint between rotatable fitting 612 and the vacuum line that does not require a separate seal such as an O-ring. Of course, an O-ring seal could also be substituted here, since there is not a concern with rigidity at this joint.

Figure 14A:
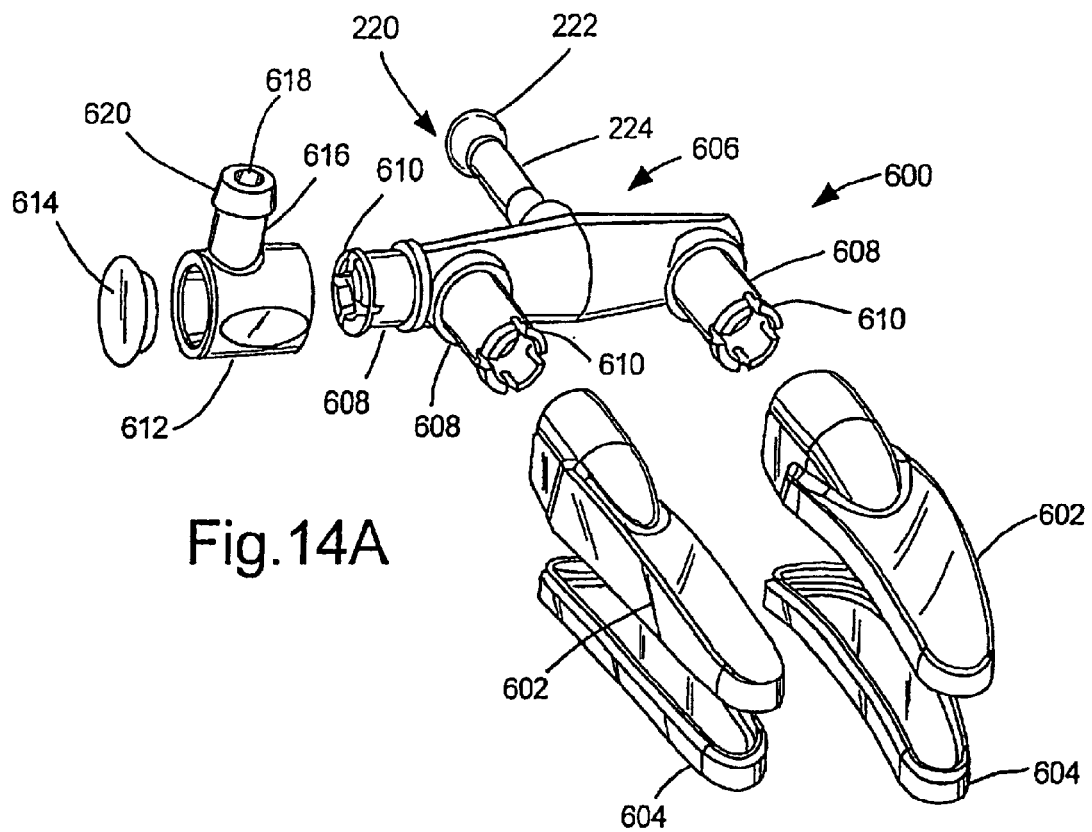
FIG. 14A is an exploded view of another example of a tissue contact member according to the present invention.
Figure 14B:
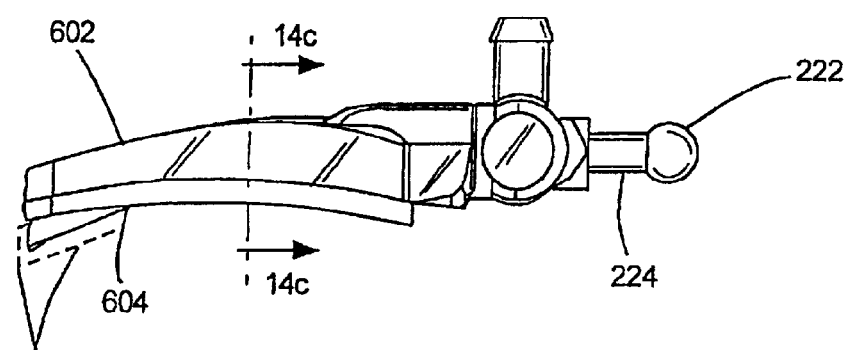
FIG. 14B is a side, assembled view of the tissue contact member shown in FIG. 14A.
Figure 14D:
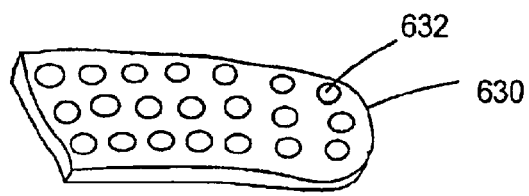
FIG. 14D is a perspective view of a porous elastic pad or filter according to the present invention.
Figure 14C:
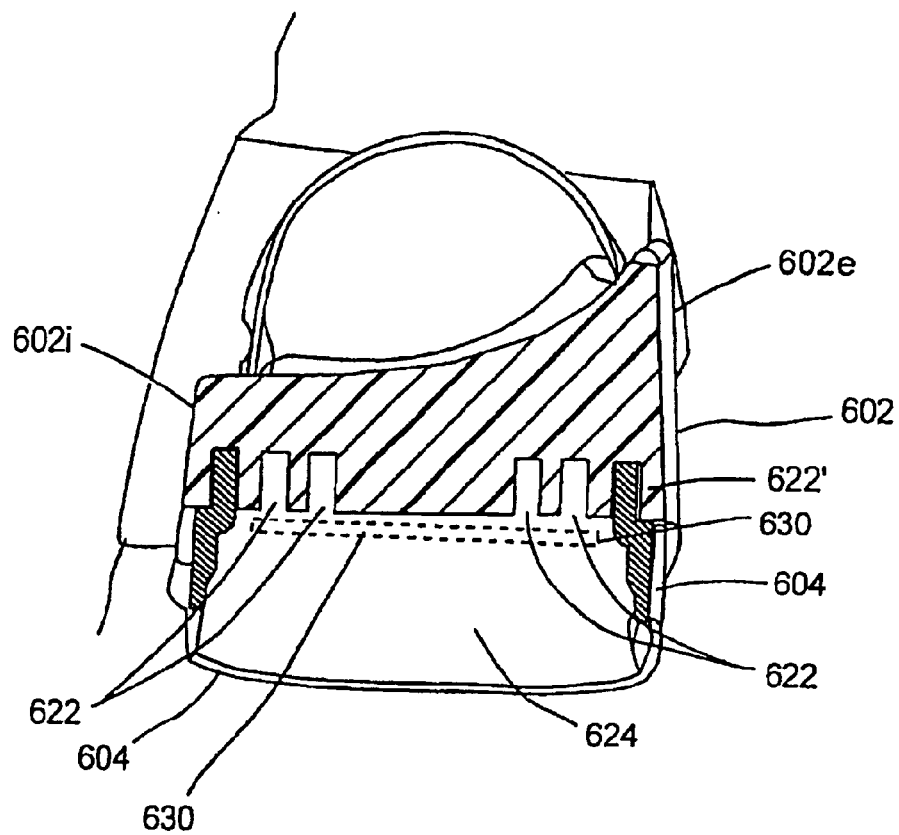
FIG. 14C is a sectional view of a foot or contact member of the tissue contact member shown in FIG. 14B, taken along line 14C—14C.

Referring to the cross-sectional view of contact member 602 shown in FIG. 14C, the contact member 602 is shown to have an asymmetrical cross section which slopes from a relatively thick external edge or ridge 602e, to a relatively thin internal side 602i. The relatively thick ridge 602e provides structural rigidity and the tapering slope conformation of the member and thin side 602i are designed to maximize the viewing and access to the target site, which is straddled by the members 602. The contact members are made of a rigid material such as polycarbonate for example. After molding the member 602, from polycarbonate, for example, compliant seal 604 is overmolded, form a material which is compatible with polycarbonate and exhibits the desired physical properties (e.g., Softflex 0615), wherein it bonds to the polycarbonate upon curing. The flexible, compliant seal 604, together with the bottom of contact member 602 defines a space 624 which is placed over the tissue to be stabilized.

Figure 14E:
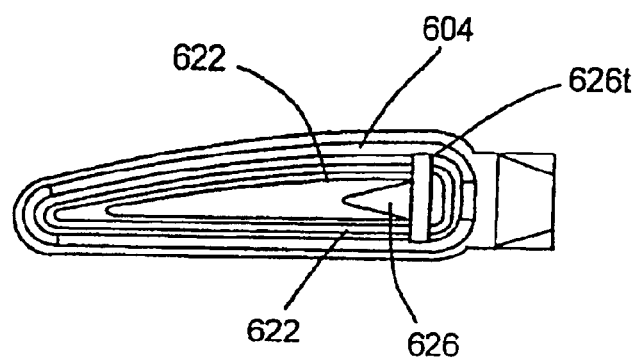
FIG. 14E is a bottom view of a foot or contact member of the tissue contact member shown in FIG. 14B.

The channels 622 are open to the space 624 and connect with deep channel 626 which fluidly connects with the manifold 606 via the opening through fitting 608. Although space 624 fluidly connects with deep channel 626, channels 622 provide additional assurance that a vacuum seal will be maintained along the length and perimeter of the contact member 602 even if tissue should be drawn up into contact with the underside of the member 602. In the example shown in FIG. 14E, the deep channel 626 extends forwardly in a teardrop configuration and also has a transverse portion 626t into which the channels 622 feed.

Optionally, an elastomeric pad or filter (shown in phantom in FIG. 14C) may be fitted or fixed against the bottom surface of the contact member 602 and covering at least a portion of the channels 622, to further ensure that a vacuum pathway remains open even if tissue is drawn up against the contact member 602. The pad 630 may be about 0.015" thick and is porous preferably having pores 632 of about 0.020" to 0.030" diameter. The pores do not necessarily have to be round in shape, but may be hexagonal, for example, or another shape. The pad may be formed of an open-cell biocompatible elastomer, such as polyurethane foam (available from Evergreen), or a closed-cell biocompatible polyurethane foam (also available from Evergreen) into which has been molded, punched, or otherwise formed pores of the above-mentioned dimensions.

Figure 14F:
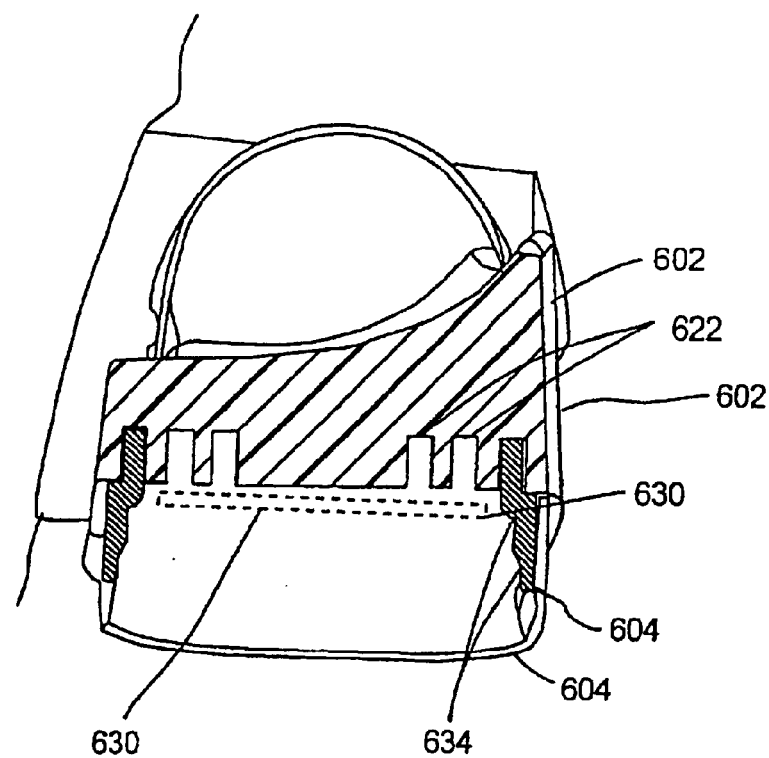
FIG. 14F is a sectional view of a foot or contact member of the tissue contact member shown in FIG. 14B, which is a variation of that shown in FIG. 14C.

FIG. 14F shows a cross section of another example of a contact member 602 which is essentially the same as that shown in FIG. 14C, except that one or more trenches 634 (in this example, two are shown) may be molded into the compliant seal 604. Trenches 634 act as living hinges when the contact member is applied to tissue and a vacuum is drawn, making the seal 604 even more flexible and compliant.

Figure 14G:
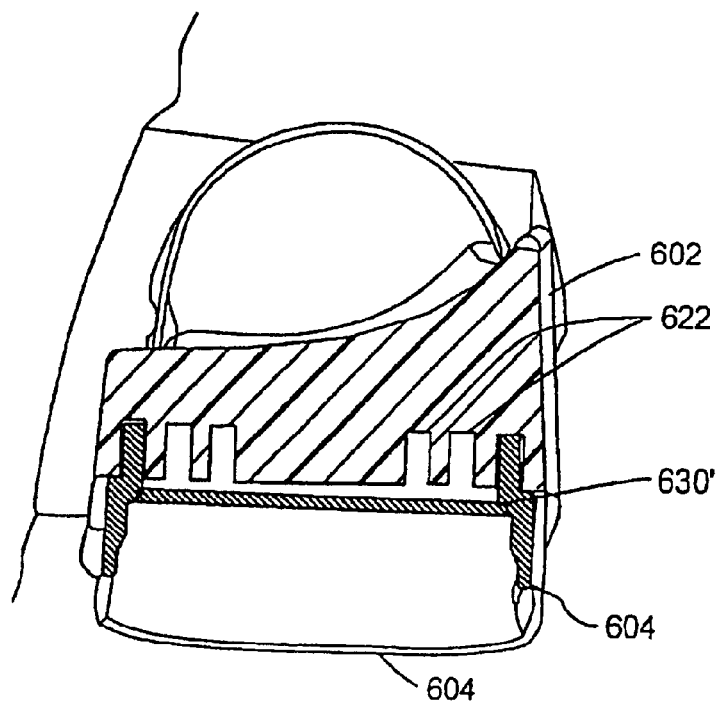
FIG. 14G is a sectional view of a foot or contact member of the tissue contact member shown in FIG. 14B, which is a variation of that shown in FIG. 14C.

FIG. 14G shows a cross section of a further example of a contact member 602 which is essentially the same as that shown in FIG. 14C, except that the porous member 630' is integrally molded with the compliant seal 604. The porous member 630' is molded at the same time and of the same material as the seal 604. Pores 632 are also molded into the porous member 630 at the same time.

Instead of an open chamber design, further alternative designs may be used in construction contact members for applying negative pressure to the tissue, such as those described in co-pending U.S. application Ser. No. 09/366, 190, filed Aug. 3, 1999 and titled "Tissue Stabilizer and Methods of Use". U.S. application Ser. No. 09/366,190 is hereby incorporated by reference in its entirety.

Figure 15A:
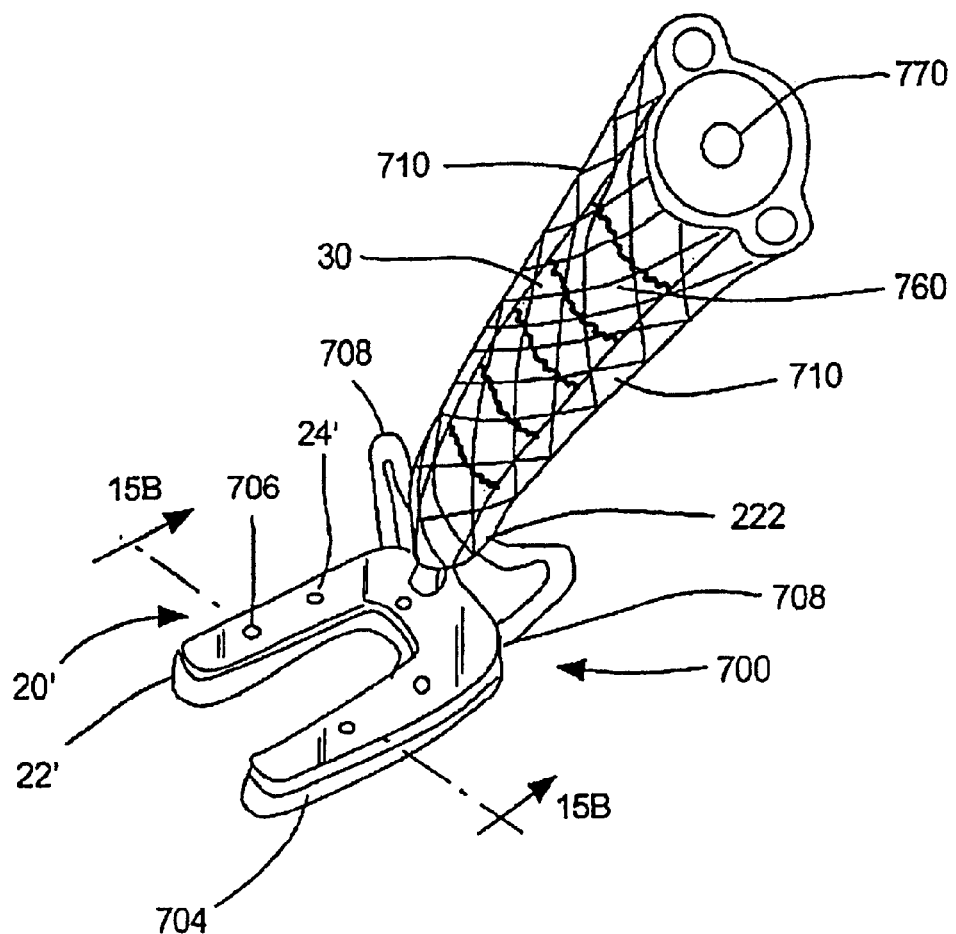
FIG. 15A is another example of a stabilizing device according to the present invention.
Figure 15B:
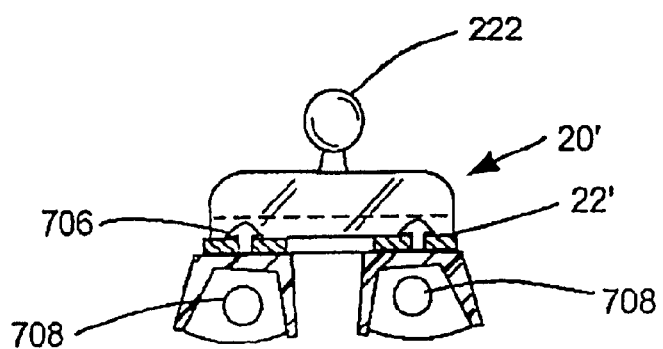
FIG. 15B is a sectional view of the tissue contact member shown in FIG. 15A, taken along line 15B—15B.

Referring now to FIG. 15A, another example of a heart contact member 700 is shown which uses negative pressure to facilitate engagement of the surface of the heart. Heart contact member 700 includes an extremely low profile member 20', which is substantially the same as contact member 20 described above, and like contact member 20, may be made from a sheet of stainless steel for example. Low profile member 20' provides the structural stiffness for the heart contact member 700 and may include a pair of feet or contact members 22', which may be substantially planar, or slightly curved to conform to the shape of the heart, or one or more may have a non-conforming curve. A compliant seal 704 extends from the bottom perimeter of the low profile member 20' (i.e., feet 22') and, when placed in contact with a tissue to be stabilized, forms an enclosed space between the tissue and the low profile member 20' within which a negative pressure can be applied, thereby sealing the sealing member 704 with the tissue. Compliant seal 704 may be fixed to the low profile member 20' by clamping, adhesives, or the like, or, in the example shown in FIG. 15A, the seal member 704 is molded with mechanical anchors 706 which are inserted through openings 24' in the low profile member 20', thereby anchoring the seal 704 to the low profile member 20'. Additionally, the seal member 704 includes one or more vacuum inlets 708 (two in the example of FIGS. 15A and 15B) into which vacuum lines are connected for application of vacuum to the space defined by the seal member 704.

In the example shown in FIG. 15A, a pair of vacuum lines 710 are connected to the heart contact member 700, as noted above. It should further be noted that any of the arrangements employing negative pressure could be so connected, and that any alternative arrangements for supplying vacuum described herein can be applied to all negative pressure embodiments of the present invention. Vacuum lines 710 run adjacent to the maneuverable arm 30 and may be maintained in position by surrounding the maneuverable arm 30 and vacuum lines 710 with a flexible sleeve 760, which may be made of an elastomer, such as silicone or dip molded PVC, for example, or preferably of a material that has more axes of elasticity, such as a knitted LYCRA® or SPANDEX material having a four or six way stretch. This maintains the vacuum lines 710 in a compact position against the sides of the links of the maneuverable arm 30, thereby ensuring that they do not obstruct the working space available to the surgeon.

Alternatively, a central opening 770 may be provided and one or more vacuum lines (not shown) may be run internally of the links of maneuverable arm 30 to make and even more compact arrangement. These lines would exit in the vicinity of the distal most flexible link, or proximal to that and connect with the seal 704 in the manner described above.

Figure 16A:
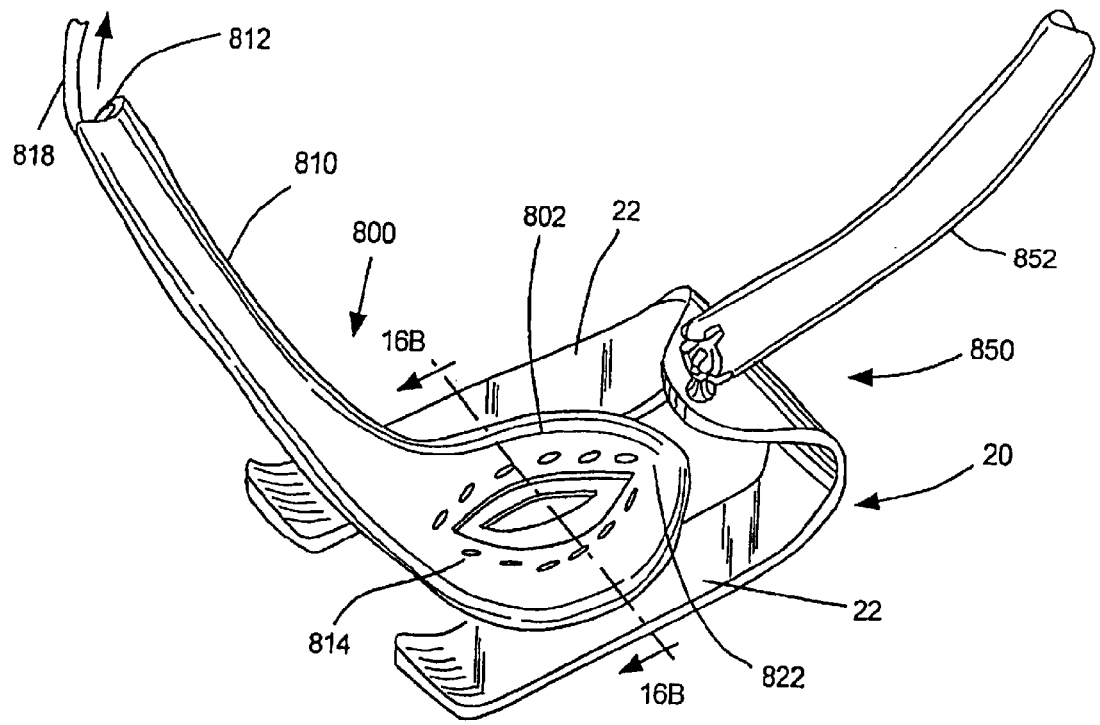
FIG. 16A is a partial perspective view of a stabilization system according to the present invention.

In some situations, an additional degree of stabilization or improved vessel presentation may be desired in the immediate vicinity of the target site where the procedure, e.g., an anastomosis, is to be performed. FIG. 16A shows a secondary stabilization device 800 which is adapted to provide additional stabilization to a region of tissue between the contact members of a primary stabilization device which are already stabilizing the general area surrounding the target site. Although secondary stabilization device 800 is shown in use with a primary stabilization device 850 which has a solid linking member 852, it is noted that secondary stabilization device 800 may be utilized with any of the primary stabilizers disclosed herein which include a multi-link maneuverable arm 30. Still further, secondary stabilization device 800 may be utilized with any primary stabilization device dimensioned to allow access by secondary contact member 802, including those primary stabilization devices which apply negative pressure through the tissue contact members.

Figure 16B:
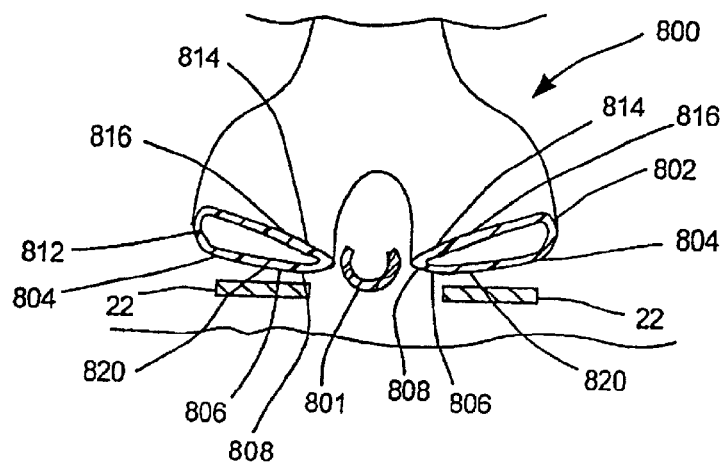
FIG. 16B is a sectional view of the tissue contact members of the stabilization system shown in FIG. 16A, taken along line 16B—16B.

Secondary contact member 802, as shown, is substantially oval shaped in a plane view but inclines or cants upwardly at its periphery in the shape of a "cowboy hat", as can be ascertained by viewing the sectional representation in FIG. 16B. This configuration enables the lower interior surfaces 806 of the secondary contact member to extend downwardly and approximate the tissue immediate adjacent a target vessel 801 while allowing the lower exterior surfaces 804 to contact the upper surfaces of primary contact members 22. Thereby further stabilizing the secondary contact member 802.

Although a mechanical secondary stabilization may be effected by simply applying a force to the tissue with secondary contact member 802, the example shown in FIG. 16A includes openings 808 adapted to apply negative pressure to the tissue contacted by secondary contact member 802. Connecting member 810 extends from secondary contact member 802 and is integrally formed therewith in this example, although a separate connecting member may be fluidly connected to secondary contact member. Connecting member 810 and secondary contact member 802 form an enclosed chamber in which negative pressure can be developed. The proximal end of connecting member 810 (not shown) is connected to a source of negative pressure. Upon application of negative pressure, openings 808 seal with the tissue, thereby drawing the tissue against the secondary contact member 802 and performing the secondary stabilization function.

Connecting member 810 may be clamped to a sternal retractor or other relatively stationary object to provide maximum rigidity or may be mounted to the primary stabilization device for simplicity or handheld. Openings 814 may be provided through the upper interior surfaces 816 of secondary contact member 802 an connected through an internal manifold 820 to a lumen 818 which runs inside of connecting member 810 and is connected to a negative or positive pressure source that is controllable independently of the negative pressure source connected to openings 808. Thus, openings 814 may be controlled to provide positive pressure, acting as a blower to blow excess blood, fluids and/or other debris away from the target site. Alternatively, openings 814 may be controlled to provide negative pressure to suction away fluids and debris from the target site.

Secondary contact member 802 may be formed of a substantially rigid polymer, such as known in the medical arts, or stainless steel, for example. In the example shown in FIG. 16A, connecting member 810 is integrally molded with secondary contact member 802, of the same material. After the anastomosis has been completed, secondary contact member may be cut at 822 or elsewhere to allow removal of the secondary stabilization member 800 from the target site. Although not necessary, secondary contact member 802 may be pre-scored to facilitate the cutting.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A system for stabilizing tissue comprising:
   a tissue contact member having a surface adapted to contact the tissue and temporarily maintain the tissue in a relatively immobilized state; and
   a maneuverable arm attached to said tissue contact member, said maneuverable arm including an articulating joint formed by a link having a male articulating surface composed of angled teeth and a female articulating surface having angled trenches adapted to receive said angled teeth, wherein said articulating joint moves in one degree of freedom directed by said angled teeth sliding against said angled trenches.

2. The system of claim 1, wherein said maneuverable arm comprises a plurality of said articulating joints.

3. The system of claim 1, further comprising a rotational joint formed by a link having a male articulating surface and a link having a female articulating surface, said male and female articulating surfaces being positioned for relative rotation in a plane perpendicular to a longitudinal axis of said maneuverable arm.

4. The system of claim 3, wherein said maneuverable arm comprises at least two of said articulating joints, at least one of said articulating joints being positioned adjacent each side of said rotational joint.

5. The system of claim 4, wherein said rotational joint comprises a first rotational joint and said tissue contact member is attached to a distal end of said maneuverable arm, said maneuverable arm further comprising a second rotational joint distally positioned adjacent said at least one articulating joint positioned adjacent a distal side of said first rotational joint.

6. The system of claim 5, wherein said second rotational joint is formed by a component have a male articulating surface and a component having a female articulating surface, said male and female articulating surfaces being positioned for relative rotation in a plane perpendicular to a longitudinal axis of said maneuverable arm.

7. The system of claim 6, wherein one of said components is a link having an articulating surface at an end opposite to said rotational joint articulating surface which is composed of angled teeth or angled trenches for articulating with a link distally adjacent said component, and wherein the other of said components comprises a mount adapted to mount said system to a fixed object.

8. The system of claim 7, wherein said mount comprises a first mount portion integral with one of said male and female articulating surfaces of said second rotational joint, and a second mount portion attached to a proximal side of said first mount portion.

9. The system of claim 8, wherein said second mount portion is pivotally attached to said first mount portion, and is pivotable away from said first mount portion to position the mount over a fixed object, or release the mount from the fixed object.

10. The system of claim 8, wherein said second mount portion is pivotable toward said first mount portion to fix said mount on the fixed object.

11. The system of claim 10, wherein said mount further comprises a locking mechanism adapted to lock said second mount portion to said first mount portion in a closed position upon pivoting said second mount portion toward said first mount portion, said closed position being configured to lock said mount on said fixed object.

12. The system of claim 11, wherein said fixed object is a sternal retractor.

13. The system of claim 12, wherein said first and second mount portions each further comprise a rail grip adapted to engage one side of a rail on said sternal retractor.

14. The system of claim 11, wherein said locking mechanism comprises a living hinge formed in one of said first and second mount portions and a pin extending transversely on the other of said first and second mount portions, said pin being adapted to snap fit into said living hinge.

15. The system of claim 8, further comprising a cable passing internally through each of said articulating joints, rotational joints and mount, said cable being further attached to a tensioning mechanism proximally of said mount.

16. The system of claim 15, wherein said tensioning mechanism comprises a screw mechanism and a knob, said screw mechanism having a first threaded component having a first set of threads and a second threaded component having a second set of threads adapted to mate with said first set of threads, said first threaded component being fixed to said cable and said knob being adapted to torque said second threaded component with respect to said first threaded component.

17. The system of claim 16, wherein said second threaded component comprises a torque limiter.

18. The system of claim 17, wherein said torque limiter further comprises a unidirectional slip clutch engaging said knob, wherein said knob positively engages said torque member for unthreading said second set of threads from said first set of threads, and positively engages said torque limiter for threading said second set of threads on said first set of threads until a predetermined amount of torque is required to further tension said cable.

19. The system of claim 18, wherein, upon reaching said predetermined amount of torque during threading, said torque limiter slips with respect to said knob.

20. The system of claim 18, wherein said slip clutch comprises at least one fin extending from an outer surface of said second threaded member at an angle to a line normal to a tangent line passing through the location from which said fin extends, each said fin adapted to engage a groove formed in an inner surface of said knob.

21. The system of claim 15, wherein said cable comprises a stop member fixed to a distal end of said cable, wherein, upon applying tension to said cable with said tensioning member, said stop member and said tensioning member apply a compressive force to said articulating joints and rotational joints, thereby locking every joint into an assumed orientation.

22. The system of claim 15, wherein said cable comprises a stop member fixed to a distal end of said cable and adapted to apply a compressive force to a distal end of said maneuverable arm when said cable is placed under tension.

23. The system of claim 22, further comprising a coupling mechanism linking said stop member to said tissue contact member, said coupling member adapted to lock said tissue contact member in an assumed position when said cable is placed under tension.

24. The system of claim 23, wherein said coupling mechanism includes a ball member fixed to said tissue contact member and a socket member rotatably joined with said stop member and adapted to receive said ball member to form a ball joint.

25. The system of claim 24, wherein said coupling mechanism further comprises a coupling link having arms adapted to lock with said socket member, and an upper abutment surface adapted to abut said stop member.

26. The system of claim 25, wherein said coupling link is a first coupling link and said coupling mechanism further comprises a second coupling link having driving surfaces adapted to contact a distal most link of a distal most articulating joint of said maneuverable arm, said second coupling link further including a lower abutment surface adapted to abut an upper portion of said ball member, wherein, upon tensioning of said cable, said stop member draws said first coupling link and said socket member in a proximal direction, whereby said socket member compresses said ball member against said lower abutment surface.

27. The system of claim 23, wherein said socket member includes a slot through a side wall thereof, said slot terminating in an enlarged opening dimensioned to permit said ball member to pass therethrough.

28. The system of claim 15, further comprising a flexible sleeve positioned over said articulating joints and said rotational joints.

29. The system of claim 28, wherein said flexible sleeve comprises an elastomer.

30. The system of claim 28, wherein said flexible sleeve comprises silicone or dip molded PVC.

31. The system of claim 28, wherein said flexible sleeve comprises a material having a four or six way stretch.

32. The system of claim 31, wherein said flexible sleeve comprises an elastomeric fabric of fibers containing polyurethane.

33. The system of claim 4, further comprising a plurality of said articulating joints on each side of said rotational joint.

34. The system of claim 33, wherein each said articulating joint is rotatable in a plane perpendicular to said plane of rotation of said rotational joint.

35. The system of claim 1, wherein said maneuverable arm is rotationally attached, at a distal end thereof to said tissue contact member.

36. The system of claim 35, wherein said tissue contact member is rotatable in three degrees of freedom with respect to said distal end of said maneuverable arm.

37. The system of claim 36, further comprising a locking mechanism for locking said tissue contact member with respect to said maneuverable arm in virtually any position to which said tissue contact member may be maneuvered when in an unlocked state.

38. The system of claim 37, wherein said locking mechanism simultaneously locks said maneuverable arm in virtually any position to which said maneuverable arm may be maneuvered when in an unlocked state.

39. The system of claim 1, wherein said tissue contact member comprises a pair of feet extending substantially parallel to one another and adapted to straddle a target site on the tissue.

40. The system of claim 39, wherein said pair of feet extend from a common base portion, said common base portion being angled away from a plane in which said feet substantially extend.

41. The system of claim 39, further comprising a ball member linked to said common base portion with a post, said ball member being adapted to form a ball joint at said distal end of said maneuverable arm.

42. The system of claim 39, wherein each of said feet has a frictional surface adapted to contact the tissue.

43. The system of claim 39, wherein each said foot comprises a thin compliant seal extending around a perimeter of a bottom surface of the respective foot.

44. The system of claim 43, wherein each said compliant seal has a tapering thickness, wherein said thickness is greater adjacent said bottom surface of said foot and tapers thinner in a direction extending away from said bottom surface.

45. The system of claim 43, wherein each said foot has a proximal end and a distal end and each said seal has a tapering length, said length measuring a distance that said seal extends away from said bottom surface of the respective foot.

46. The system of claim 45, wherein said length of each said seal is greater near said proximal end of said foot than near said distal end of said foot.

47. The system of claim 43, wherein each said seal comprises compliant thermoplastic urethane.

48. The system of claim 39, wherein said tissue contact member further comprises a manifold base interconnected with said pair of feet, said manifold base being substantially hollow and having a pair of fittings extending therefrom, said feet being mounted on said fittings.

49. The system of claim 48, wherein each fitting has an opening therethrough which fluidly connects said respective foot with said manifold base.

50. The system of claim 49, wherein each said foot has a hollow interior defining a vacuum chamber, each said vacuum chamber having a first opening adapted to engage at least a portion of said tissue and a second opening fluidly coupled with said opening through said respective fitting.

51. The system of claim 50, wherein said vacuum chamber further comprises channels formed on an upper interior surface of each said foot.

52. The system of claim 51, wherein said channels are aligned substantially parallel to one another and extend in a direction said proximal end to said distal end of said foot.

53. The system of claim 52, further comprising a deep channel near said distal end of each said foot, said deep channel fluidly communicating with said opening through said fitting, respectively.

54. The system of claim 52, wherein each said foot comprises a thin compliant seal extending around a perimeter of a bottom surface of the respective foot and integrally molded in a pair of said channels nearest said perimeter.

55. The system of claim 54, wherein each said seal is provided with one or more grooves to further enhance the flexibility of said seal.

56. The system of claim 52, further comprising a porous filter covering at least a portion of said channel.

57. The system of claim 56, wherein each said foot comprises a thin compliant seal extending around a perimeter of a bottom surface of the respective foot and said porous filter is integrally molded with said thin compliant seal, respectively.

58. The system of claim 49, wherein each said fitting has an enlarged lip and said feet are adapted to snap fit over said enlarged lips, thereby substantially sealing said feet with said fittings without the need for an O-ring or other additional sealing member therebetween.

59. The system of claim 48, wherein each said foot is independently rotatable about said respective fitting.

60. The system of claim 48, wherein each said foot has an asymmetrical transverse cross-section, a portion of said cross-section further from the other of said feet being thicker than a portion nearer to the other of said feet, to provide more available space between said feet.

61. The system of claim 48, further comprising a third fitting extending from said manifold base, said third fitting an opening therethrough which is adapted to connect said manifold base with a vacuum source.

62. The system of claim 61, further comprising a rotatable fitting adapted to snap fit over said third fitting, said rotatable fitting further comprising an inlet tube configured for connecting with a vacuum line, whereby the vacuum line is rotatably mounted to said manifold base.

63. The system of claim 39, wherein said pair of feet extend from a common base portion, and a ball member is linked to said common base portion with a post, said ball member being adapted to form a ball joint at said distal end of said maneuverable arm.

64. The system of claim 63, wherein each of said pair of feet comprises an extremely low profile structural member and a thin compliant seal extending from a bottom perimeter of said structural member.

65. The system of claim 64, wherein each said thin compliant seal comprises a vacuum inlet adapted to connect with a vacuum line.

66. The system of claim 64, wherein said extremely low profile structural member is formed from a sheet of stainless steel.

67. A maneuverable arm adapted to position a surgical tool mounted at a distal end thereof in a variety of orientations, said maneuverable arm comprising:
at least one articulating joint formed by a link having a male articulating surface composed of angled teeth and a female articulating surface having angled trenches adapted to receive said angled teeth, wherein said articulating joint moves in one degree of freedom directed by said angled teeth sliding against said angled trenches.

68. The maneuverable arm of claim 67, wherein said trenches have an aspect ratio of at least about 1:2.

69. The maneuverable arm of claim 68, wherein said aspect ration of said trenches is about 1:1.

70. The maneuverable arm of claim 67, wherein said teeth have an aspect ratio of at least about 1:2.

71. The maneuverable arm of claim 70, wherein said aspect ration of said teeth is about 1:1.

72. The maneuverable arm of claim 67, wherein said at least one articulating joint comprises a plurality of said articulating joints.

73. The maneuverable arm of claim 72, further comprising a cable extending internally through each of said articulating joints, said cable having a stop member at a distal end thereof, said maneuverable arm further comprising an anchor fixed to a proximal end of said cable, wherein each of said articulating joints are sequentially held together in approximation by said cable, stop member and anchor.

74. The maneuverable arm of claim 73, further comprising a mount adjacent a proximal most of said articulating joints, said cable passing through said mount and said mount being approximated with said articulating joints by said anchor.

75. The maneuverable arm of claim 74, further comprising a rotational joint formed by a link having a male articulating surface and a link having a female articulating surface, said male and female articulating surfaces being positioned for relative rotation in a plane perpendicular to a longitudinal axis of said maneuverable arm.

76. The maneuverable arm of claim 75, wherein said rotational joint is positioned between a pair of said articulating joints.

77. The maneuverable arm of claim 76, wherein said link of said rotational joint having a male articulating surface has an articulating surface at an opposite end thereof which comprises trenches or teeth for articulating with said adjacent articulating joint, and wherein said link of said rotational joint having a female articulating surface has an articulating surface at an opposite end thereof which comprises trenches or teeth for articulating with said adjacent articulating joint.

78. The maneuverable arm of claim 75, wherein said rotational joint is positioned between a proximal most one of said articulating links and said mount, and wherein said male or female articulating surface of said rotational joint is integral with said mount.

79. The maneuverable arm of claim 78, wherein said male articulating surface of said rotational joint is integral with said mount.

80. The maneuverable arm of claim 83, wherein said rotational joint is positioned as an end joint of said maneuverable arm.

81. The maneuverable arm of claim 74, wherein said mount comprises a first mount portion adjacent said proximal most of said articulating joints, and a second mount portion attached to a proximal side of said first mount portion.

82. The maneuverable arm of claim 81, wherein said second mount portion is pivotally attached to said first mount portion, and is pivotable away from said first mount portion to position the mount over a fixed object, or release the mount from the fixed object.

83. The maneuverable arm of claim 81, wherein said second mount portion is pivotable toward said first mount positioned to fix said mount on the fixed object.

84. The maneuverable arm of claim 83, wherein said mount further comprises a locking mechanism adapted to lock said second mount portion to said first mount portion in a closed position upon pivoting said second mount portion toward said first mount portion, said closed position being configured to lock said mount on said fixed object.

85. The maneuverable arm of claim 84, wherein said fixed object is a sternal retractor.

86. The maneuverable arm of claim 85, wherein said first and second mount portions each further comprise a rail grip adapted to engage one side of a rail on said sternal retractor.

87. The maneuverable arm of claim 84, wherein said locking mechanism comprises a living hinge formed in one of said first and second mount portions and a pin extending transversely on the other of said first and second mount portions, said pin being adapted to snap fit into said living hinge.

88. The maneuverable arm of claim 74, further comprising a tensioning mechanism connected proximally of said mount, wherein said tensioning mechanism comprises a screw mechanism and a knob, said screw mechanism having a first threaded component having a first set of threads and a second threaded component having a second set of threads adapted to mate with said first set of threads, said first threaded component being fixed to said cable and said knob being adapted to torque said second threaded component with respect to said first threaded component.

89. The maneuverable arm of claim 88, wherein said second threaded component comprises a torque limiter.

90. The maneuverable arm of claim 89, wherein said torque limiter further comprises a unidirectional slip clutch engaging said knob, wherein said knob positively engages said torque member for unthreading said second set of threads from said first set of threads, and positively engages said torque limiter for threading said second set of threads on said first set of threads until a predetermined amount of torque is required to further tension said cable.

91. The maneuverable arm of claim 90, wherein, upon reaching said predetermined amount of torque during threading, said torque limiter slips with respect to said knob.

92. The maneuverable arm of claim 90, wherein said slip clutch comprises at least one fin extending from an outer surface of said second threaded member at an angle to a line normal to a tangent line passing through the location from which said fin extends, each said fin adapted to engage a groove formed in an inner surface of said knob.

93. The maneuverable arm of claim 88, wherein, upon applying tension to said cable with said tensioning member, said stop member and said tensioning member apply a compressive force to said maneuverable arm, thereby locking every joint into an assumed orientation.

94. The maneuverable arm of claim 73, further comprising a rotational joint formed by a link having a male articulating surface and a link having a female articulating surface, said male and female articulating surfaces being positioned for relative rotation in a plane perpendicular to a longitudinal is of said maneuverable arm.

95. The maneuverable arm of claim 94, wherein said rotational joint is positioned between a pair of said articulating joints.

96. The maneuverable arm of claim 95, wherein said link of said rotational joint having a male articulating surface has an articulating surface at an opposite end thereof which comprises trenches or teeth for articulating with said adjacent articulating joint, and wherein said link of said rotational joint having a female articulating surface has an articulating surface at an opposite end thereof which comprises trenches or teeth for articulating with said adjacent articulating joint.

97. The maneuverable arm of claim 94, wherein said rotational joint is positioned as an end of said maneuverable arm.

98. A tensioning mechanism for applying tension to a cable passing through a maneuverable surgical instrument having at least one articulating joint through which the cable passes, said tensioning mechanism comprising a screw mechanism and a knob, said screw mechanism having a first threaded component having a first set of threads and a second threaded component having a second set of threads adapted to mate with said first set of threads, said first threaded component being fixed to said cable and said second threaded component comprising a torque limiter, said knob being adapted to torque said second threaded component with respect to said first threaded component.

99. The mechanism of claim 98, wherein said torque limiter further comprises a unidirectional slip clutch engaging said knob, wherein said knob positively engages said torque member for unthreading said second set of threads from said first set of threads, and positively engages said torque limiter for threading said second set of threads on said first set of threads until a predetermined amount of torque is required to further tension said cable.

100. The mechanism of claim 99, wherein, upon reaching said predetermined amount of torque during threading, said torque limiter slips with respect to said knob.

101. The mechanism of claim 99, wherein said slip clutch comprises at least one fin extending from an outer surface of said second threaded member at an angle to a line normal to a tangent line passing through the location from which said fin extends, each said fin adapted to engage a groove formed in an inner surface of said knob.

102. The mechanism of claim 98, wherein, upon torquing said second threaded component with respect to said first threaded component, said cable is drawn under tension.

* * * * *